United States Patent
Udd

(10) Patent No.: US 8,780,339 B2
(45) Date of Patent: Jul. 15, 2014

(54) FIBER SHAPE SENSING SYSTEMS AND METHODS

(75) Inventor: Eric Udd, Fairview, OR (US)

(73) Assignee: Koninklijke Philips N.V., Eindhoven (NL)

(*) Notice: Subject to any disclaimer, the term of this patent is extended or adjusted under 35 U.S.C. 154(b) by 472 days.

(21) Appl. No.: 12/837,440

(22) Filed: Jul. 15, 2010

(65) Prior Publication Data

US 2011/0090486 A1    Apr. 21, 2011

Related U.S. Application Data

(60) Provisional application No. 61/225,883, filed on Jul. 15, 2009.

(51) Int. Cl.
*G01N 21/00* (2006.01)
*G02B 6/00* (2006.01)

(52) U.S. Cl.
USPC .......................................... 356/73.1; 385/13

(58) Field of Classification Search
None
See application file for complete search history.

(56) References Cited

U.S. PATENT DOCUMENTS

| | | | |
|---|---|---|---|
| 3,807,390 A | 4/1974 | Ostrowski et al. |
| 4,443,698 A | 4/1984 | Schiffner |
| 4,761,073 A | 8/1988 | Meltz et al. |
| 4,960,410 A | 10/1990 | Pinchuk |
| 4,996,419 A | 2/1991 | Morey |
| 5,007,705 A | 4/1991 | Morey et al. |
| 5,066,133 A | 11/1991 | Brienza |
| 5,118,931 A | 6/1992 | Udd et al. |
| 5,144,690 A | 9/1992 | Domash |
| 5,267,339 A | 11/1993 | Yamauchi et al. |
| 5,380,995 A | 1/1995 | Udd et al. |
| 5,397,891 A | 3/1995 | Udd et al. |
| 5,401,956 A | 3/1995 | Dunphy et al. |
| 5,492,131 A | 2/1996 | Galel |
| 5,563,967 A | 10/1996 | Haake |
| 5,591,965 A | 1/1997 | Udd |
| 5,627,927 A | 5/1997 | Udd |
| 5,630,783 A | 5/1997 | Steinberg |
| 5,798,521 A | 8/1998 | Froggatt |
| 5,828,059 A | 10/1998 | Udd |
| 5,917,978 A | 6/1999 | Rutterman |
| 6,035,082 A | 3/2000 | Murphy et al. |
| 6,069,420 A | 5/2000 | Mizzi et al. |
| 6,144,026 A | 11/2000 | Udd et al. |

(Continued)

FOREIGN PATENT DOCUMENTS

| WO | WO 92/02276 | 2/1992 |
|---|---|---|
| WO | WO 01/33165 | 5/2001 |

(Continued)

OTHER PUBLICATIONS

Eric Udd, "Good Sense", Spie's OE Magazine, Aug. 2002, pp. 27-30.

(Continued)

*Primary Examiner* — Gordon J Stock, Jr.

(57) ABSTRACT

In certain variations, fiber shape sensing or measuring systems, devices and methods are described herein, which allow for measurement of three dimensional bending as well as twist measurements of various fibers, e.g., optical fibers and fiber optic probes of various sizes. In certain variations, the systems are designed to take advantage of unique light guiding properties of optical fibers and various fiber gratings.

68 Claims, 24 Drawing Sheets

(56) References Cited

U.S. PATENT DOCUMENTS

| | | | |
|---|---|---|---|
| 6,215,943 B1 | 4/2001 | Crotts et al. | |
| 6,256,090 B1 | 7/2001 | Chen et al. | |
| 6,275,511 B1 | 8/2001 | Pan et al. | |
| 6,275,628 B1 | 8/2001 | Jones et al. | |
| 6,301,420 B1 | 10/2001 | Greenaway | |
| 6,366,722 B1 | 4/2002 | Murphy et al. | |
| 6,389,187 B1 | 5/2002 | Greenaway et al. | |
| 6,404,956 B1 | 6/2002 | Brennan, III et al. | |
| 6,426,796 B1 | 7/2002 | Pulliam et al. | |
| 6,470,205 B2 | 10/2002 | Bosselmann et al. | |
| 6,471,710 B1 | 10/2002 | Bucholtz | |
| 6,545,760 B1 | 4/2003 | Froggatt et al. | |
| 6,563,107 B2* | 5/2003 | Danisch et al. | 250/227.14 |
| 6,571,639 B1 | 6/2003 | May et al. | |
| 6,611,700 B1 | 8/2003 | Vilsmeier et al. | |
| 6,671,055 B1 | 12/2003 | Wavering et al. | |
| 6,716,178 B1 | 4/2004 | Kilpatrick et al. | |
| 6,796,963 B2 | 9/2004 | Carpenter et al. | |
| 6,826,343 B2 | 11/2004 | Davis et al. | |
| 6,876,786 B2 | 4/2005 | Chliaguine et al. | |
| 6,888,623 B2 | 5/2005 | Clements | |
| 6,898,337 B2 | 5/2005 | Averett et al. | |
| 6,923,048 B2 | 8/2005 | Willsch et al. | |
| 6,950,570 B1* | 9/2005 | Novotny | 385/18 |
| 6,965,708 B2 | 11/2005 | Luo et al. | |
| 6,974,455 B2 | 12/2005 | Garabedian et al. | |
| 6,987,897 B2 | 1/2006 | Elster et al. | |
| 7,010,182 B2 | 3/2006 | Pennington | |
| 7,038,190 B2 | 5/2006 | Udd et al. | |
| 7,042,573 B2 | 5/2006 | Froggatt | |
| 7,046,866 B2 | 5/2006 | Sahlgren et al. | |
| 7,154,081 B1 | 12/2006 | Friedersdorf et al. | |
| 7,330,245 B2 | 2/2008 | Froggatt | |
| 7,538,883 B2 | 5/2009 | Froggatt | |
| 7,561,276 B2 | 7/2009 | Boyd | |
| 7,772,541 B2 | 8/2010 | Froggatt et al. | |
| 7,781,724 B2 | 8/2010 | Childers | |
| 7,789,875 B2 | 9/2010 | Brock et al. | |
| 2001/0021843 A1 | 9/2001 | Bosselmann et al. | |
| 2003/0016898 A1* | 1/2003 | Baruch et al. | 385/12 |
| 2004/0165810 A1 | 8/2004 | Fujita | |
| 2005/0036140 A1 | 2/2005 | Elster et al. | |
| 2005/0054934 A1 | 3/2005 | Furnish et al. | |
| 2005/0137478 A1 | 6/2005 | Younge et al. | |
| 2005/0197530 A1 | 9/2005 | Wallace et al. | |
| 2005/0201664 A1 | 9/2005 | Udd et al. | |
| 2005/0222554 A1 | 10/2005 | Wallace et al. | |
| 2006/0013523 A1 | 1/2006 | Childers et al. | |
| 2006/0036164 A1 | 2/2006 | Wilson et al. | |
| 2006/0036213 A1 | 2/2006 | Viswanathan | |
| 2006/0057560 A1 | 3/2006 | Hlavka et al. | |
| 2006/0084945 A1 | 4/2006 | Moll et al. | |
| 2006/0095022 A1 | 5/2006 | Moll et al. | |
| 2006/0100610 A1 | 5/2006 | Wallace et al. | |
| 2006/0111692 A1 | 5/2006 | Hlavka et al. | |
| 2006/0200026 A1 | 9/2006 | Wallace et al. | |
| 2006/0200049 A1 | 9/2006 | Leo et al. | |
| 2006/0253108 A1 | 11/2006 | Yu et al. | |
| 2006/0276775 A1 | 12/2006 | Rosenberg et al. | |
| 2007/0043338 A1 | 2/2007 | Moll et al. | |
| 2007/0060847 A1 | 3/2007 | Leo et al. | |
| 2007/0156019 A1 | 7/2007 | Larkin et al. | |
| 2007/0156123 A1 | 7/2007 | Moll et al. | |
| 2007/0161857 A1 | 7/2007 | Durant et al. | |
| 2007/0197896 A1 | 8/2007 | Moll et al. | |
| 2007/0197939 A1 | 8/2007 | Wallace et al. | |
| 2007/0233044 A1 | 10/2007 | Wallace et al. | |
| 2007/0265503 A1 | 11/2007 | Schlesinger | |
| 2008/0009750 A1 | 1/2008 | Aeby et al. | |
| 2008/0212082 A1* | 9/2008 | Froggatt et al. | 356/73.1 |
| 2008/0218770 A1 | 9/2008 | Moll | |
| 2008/0243064 A1 | 10/2008 | Stahler et al. | |
| 2008/0249536 A1 | 10/2008 | Stahler et al. | |
| 2008/0262480 A1 | 10/2008 | Stahler et al. | |
| 2008/0262513 A1 | 10/2008 | Stahler et al. | |
| 2008/0285909 A1* | 11/2008 | Younge et al. | 385/13 |
| 2009/0123111 A1 | 5/2009 | Udd | |
| 2009/0138025 A1 | 5/2009 | Stahler et al. | |
| 2009/0201503 A1* | 8/2009 | Bennion et al. | 356/370 |
| 2009/0320527 A1* | 12/2009 | Harper et al. | 65/381 |
| 2010/0114115 A1 | 5/2010 | Schlesinger et al. | |
| 2012/0281205 A1* | 11/2012 | Askins | 356/73.1 |

FOREIGN PATENT DOCUMENTS

| | | |
|---|---|---|
| WO | WO 02/47751 | 6/2002 |
| WO | WO 03/065095 | 8/2003 |
| WO | WO 2004/001469 | 12/2003 |
| WO | WO 2005/087128 | 9/2005 |
| WO | WO 2006/092707 | 9/2006 |
| WO | WO 2006/099056 | 9/2006 |
| WO | WO 2008/094949 | 8/2008 |
| WO | WO 2008/131303 | 10/2008 |

OTHER PUBLICATIONS

G.M.H. Flockhart et al., "Two-axis bend measurement with Bragg gratings in multicore optical fiber", Optics Letters, Mar. 15, 2003, pp. 387-389, vol. 28 No. 6, Optical Society of America.

File history of U.S. Patent No. 6,256,090, (U.S. Appl. No. 09/127,083), issued on Jul. 3, 2001.

File history of U.S. Patent No. 6,470,205, (U.S. Appl. No. 09/804,804), issued on Oct. 22, 2002.

File History of U.S. Patent No. 5,798,521, (U.S. Appl. No. 08/086,732) issued on Aug. 25 1998.

Alan D. Kersey et al., "Fiber Grating Sensors", Journal of Lightwave Technology, Aug. 1997, pp. 1442-1463 vol. 15 No. 8.

Mark Froggatt et al., "Distributed measurement of static strain in an optical fiber with multiple Bragg gratings at nominally equal wavelengths", Applied Optics, Apr. 1, 1998, pp. 1741-1746, vol. 37 No. 10.

Raymond M. Measures, "Fiber Optic Strain Sensing", Fiber Optic Smart Structures, 1995, pp. 171-247, John Wiley & Sons Inc.

C.M. Lawrence et al., "A Fiber Optic Sensor for Transverse Strain Measurement", Experimental Mechanics, Sep. 1999, pp. 202-209, vol. 39 No. 3.

File history of U.S. Appl. No. 11/450,072, filed Jun. 9, 2006, published as 2008-0009750, on Jan. 10, 2008.

Meng-Chou Wu et al., "Fabrication of self-apodized short-length fiber Bragg gratings", Applied Optics, Sep. 1, 2003, pp. 5017-5023, vol. 42, No. 25.

Kenneth O. Hill et al., "Fiber Bragg Grating Technology Fundamentals and Overview", Journal of Lightwave Technology, Aug. 1997, pp. 1263-1276, vol. 15 No. 8.

Yan Zhang et al., "Fiber-Bragg-grating-based seismic geophone for oil/gas prospecting", Optical Engineering, Aug. 2006, pp. 84404-1-84404-4, vol. 45 No. 8.

Mark E. Froggatt et al., "Distributed Fiber-Optic Strain and Temperature Sensors Using Photoinduced Bragg Gratings", Feb. 1995, pp. 1741-1746, Blacksburg Virginia.

Claire Davis, "Strain Survey of an F/A-18 Stabilator Spindle Using High Density Bragg Grating Arrays", Feb. 2005, Australia.

Zhang Lun-Wei, "Novel shape detection systems based on FBG sensor net for intelligent endoscope", Journal of Shanghai University (English Edition), Apr. 2006, pp. 154-155, vol. 10 No. 2.

V.V. Wong et al., "Distributed Bragg grating integrated-optical filters: Synthesis and fabrication", American Vacuum Society, Nov./Dec. 1995, pp. 2859-2864, vol. 13 No. 6.

Youngmin Kim et al., "Micromachined Fabry-Perot Cavity Pressure Transducer", IEEE Photonics Technology Letters, Dec. 1995, pp. 1471-1473, vol. 7 No. 12.

John W. Berthold III, "Historical Review of Microbend Fiber-Optic Sensors", Journal of Lightwave Technology, Jul. 1995, pp. 1193-1199, vol. 13 No. 7.

R. Posey Jr. et al., "Strain sensing based on coherent Rayleigh scattering in an optical fibre", Electronics Letters, Sep. 28, 2000, pp. 1688-1689, vol. 36 No. 20.

Kazuo Hotate et al., "Proposal and experimental verification of Bragg wavelength distribution measurement within a long-length FBG by

(56) References Cited

OTHER PUBLICATIONS synthesis of optical coherence function" Optics Express, May 26, 2008, pp. 7881-7887, vol. 16 No. 11.

M.M. Ohn et al., "Arbitrary strain profile measurement within fibre gratings using interferometric Fourier transform technique", Electronics Letters, Jul. 3, 1997, pp. 1242-1243, vol. 33 No. 14.

Zhang Lunwei et al., "FBG Sensor Devices for Spatial Shape Detection of Intelligent Colonscope", Apr. 2004, pp. 835-840, New Orleans Louisiana.

Craig M. Lopatin et al., "Distributed Measurement of Strain in Smart Materials Using Rayleigh Scattering", 32 International SAMPE Technical Conference, Nov. 2000, pp. 231-241.

X.G. Tian et al., "Torsion Measurement Using Fiber Bragg Grating Sensors", Experimental Mechanics, Sep. 2001, pp. 248-253, vol. 41 No. 3.

Garret Lee et al., "Intraoperative Use of Duel Fiberoptic Catheter for Simultaneous In Vivo Visualization and Laser Vaporization of Peripheral Atherosclerotic Obstructive Disease", Catheterization and Cardiovascular Diagnosis, 1984, pp. 11-16.

Mark Froggatt et al., "High-spatial-resolution distributed strain measurement in optical fiber with Rayleigh scatter", Applied Optics, Apr. 1, 1998, pp. 1735-1740, vol. 37 No. 10.

Gary A. Miller et al., "Shape Sensing Using Distributed Fiber Optic Strain Measurements", Second European Workshop on Optical Fibre Sensors, Proceedings of the SPIE, Jun. 2004, pp. 528-531, vol. 5502.

M. J. Gander et al., "Measurement of bending in two dimensions using multicore optical fibre", European Workshop on Optical Fibre Sensors, Jun. 1998, p. 64-68, Proc. SPIE vol. 3483.

Ad A. M. Maas, "Shape measurement using phase shifting speckle interferomentry", Laser Interferometry IV: Computer-Aided Interferometry, Jan. 1, 1992, pp. 558-568, Proceedings SPIE vol. 1553.

Roger R. Duncan et al., "Use of high spatial resolution fiber-optic shape sensors to monitor the shape of deployable space structures" Space Technology and Applications Int.Forum-Staif 2005: Conf. Thermophys in Micrograv;Conf Comm/Civil Next Gen.Space Transp; 22nd Symp Space Nucl.Powr Propuls.;Conf.Human/Robotic Techn.Nat'l Vision Space Expl.; 3rd Symp Space Colon.; 2nd Symp. New Frontiers. AIP Conference Proceedings, Feb. 2005, pp. 880-886, vol. 746.

Joeseph R. Blandino et al., "Three-dimensional shape sensing for inflatable booms", 46th AIAA/ASME/ASCE/AHS/ASC Structures, Structural Dynamics & Materials Conference, Austin, Texas, Conference Dates : Apr. 18-21, 2005, pp. 1-10.

Roger R. Duncan et al., "Characterization of a fiber optic shape and position sensor" Conference Title: Smart Structures and Materials 2006: Smart Sensor Monitoring Systems and Applications; San Diego, CA, Conference Date: Monday Feb. 27, 2006, Published in: Proc. SPIE, vol. 6167, 616704 (2006); doi:10.1117/12.658535, Online Publication Date: Mar. 30, 2006.

Roger R. Duncan et al., "High-accuracy fiber-optic shape sensing" Conference Title: Sensor Systems and Networks: Phenomena, Technology, and Applications for NDE and Health Monitoring 2007, San Diego, California, USA, Conference Date: Monday Mar. 19, 2007, Published in: Proc. SPIE, vol. 6530, 65301S (2007); doi:10.1117/12.720914, Online Publication Date: Apr. 10, 2007.

Eric Udd et al., "Progress on developing a multiaxis fiber optic strain sensor" Third Pacific Northwest Fiber Optic Sensor Workshop, Publication Date: Sep. 2, 1997, pp. 50-56, Proceedings SPIE vol. 3180.

Eric Udd et al., "Multidimensional strain field measurements using fiber optic grating sensors", Smart Structures and Materials 2000: Sensory Phenomena and Measurement Instrumentation for Smart Structures and Materials, Publication Date: Jun. 12, 2000, pp. 254-262, Proceedings SPIE vol. 3986.

Juncheng Xu et al., "Miniature fiber optic pressure and temperature sensors", Fiber Optic Sensor Technology and Applications IV, Publication Date: Nov. 10, 2005, pp. 600403-1-600403-6, Proceedings SPIE vol. 6004.

M. Lequime et al., "Fiber optic pressure and temperature sensor for down-hole applications", , Fiber Optic Sensors: Engineering and Applications, Publication Date: Aug. 1, 1991, pp. 244-249, Proceedings SPIE vol. 1511.

T. Sato et al., "Ground strain measuring system using optical fiber sensors", Smart Structures and Materials 2000: Sensory Phenomena and Measurement Instrumentation for Smart Structures and Materials, Publication Date: Jun. 12, 2000, pp. 180-190, Proceedings SPIE vol. 3986.

Mark Froggatt, Intracore and extracore examination of fiber gratings with coherent, Thesis (PhD). The University of Rochester, Jun. 2001, pp. 6540, Source DAI-B 61/12.

J. Grant et al., "Investigation of structural properties of carbon-epoxy composites using fiber-bragg gratings", Applications of Photonic Technology 5, Publication Date: Feb. 17, 2003, pp. 191-199, Proceedings SPIE vol. 4833.

Roger R. Duncan et al., "A distributed sensing technique for aerospace applications", 42nd AIAA Aerospace Sciences Meeting and Exhibit, Conference dates: Jan. 5-8, 2004, Reno, Nevada.

S. Huang et al., "Continuous arbitrary strain profile measurements with fiber bragg gratings", Smart Materials and Structures, Publication Date: Apr. 1998, pp. 248-256, vol. 7, No. 2.

Youngmin Kim et al., "Design for manufacture of micromachined Fabry-Perot cavity-based sensors", Sensors and actuators. A, Physical, ISSN 0924-4247, 1995, pp. 141-146 [(article)], vol. 50, n° 1-2.

Eric Pinet et al., "True challenges of disposable optic fiber sensors for clinical environment", Third European Workshop on Optical Fibre Sensors, Antonello Cutolo; Brian Culshaw; José Miguel López-Higuera, Editors, 66191Q, Publication Date: Jul. 2, 2007, pp. 66191Q-1-66191Q-4, Proceedings SPIE vol. 6619.

Brian J. Soller et al., "Optical frequency domain reflectometry for single- and multi-mode avionics fiber-optics applications", Avionics Fiber-Optics and Photonics, Publication Date: Sep. 12-14, 2006, pp. 38-39, IEEE Conference.

Jin-Seok Heo et al., "Design of TR-EFPI fiber optic pressure sensor for the medical application", International Journal of Human-friendly Welfare Robotic Systems, Published : 2002, pp. 2-7, vol. 3, No. 2.

Matt Raum et al "Performance Analysis of a Fiber-Optic Shape Sensing Systems" cited as reference of 'Fiber-optic shape sensing and distributed strain measurements on a morphing chevron', Collection of Technical papers—44th AIAA, vol. 10, 2006, pp. 7460-7482.

Distributed Sensing System Sensor Array Specification, www.lunainnovations.com, pp. 1-3.

Kirby et al, "Optimal sensor layout for shape estimation form strain sensors", Smart Structures and Materials, Mar. 1995, pp. 367-376, Proc. SPIE vol. 2444.

Maas, "Shape Measurement using phase shifting speckle interferometry", Laser Interferometry IV, Jan. 1992, pp. 558-568, SPIE vol. 1553.

Davis et al, "Fiber-optic bragg grating array for shape and vibration mode sensing", May 1994, pp. 94-102, Proceedings SPIE vol. 2191.

Gander et al, "Bend Measurement using multicore optical fiber", Proceedings of OFS-12, Oct. 1997, pp. 166-169.

Kreger et al, "Distributed strain and temperature sensing in plastic optical fiber using Rayleigh scattering", Apr. 2009, pp. 73160A-1-73160A-8, Proc. of SPIE 7316.

Kreger et al, "High-resolution extended distance distributed fiber-optic sensing using Rayleigh backscatter", Apr. 2007, pp. 65301R-1-65301R-10, Proc. of SPIE vol. 6530.

Danisch et al, "Spatially continuous six degree of freedom position and orientation sensor", Sensor Review, 1999, pp. 106-112, vol. 19.

Gifford et al, "Swept-wavelength interferometric interrogation of fiber Rayleigh scatter for distributed sensing applications", 2007, pp. 67700F-1-67700F-9, Proc. of SPIE col. 6770.

Miller et al, "Fiber-optic shape sensing for flexible structures", Feb. 1989, pp. 399-404, SPIE 1170.

Morey, "Fiber-optic bragg grating sensors", 1989, pp. 98-107, SPIEL col. 1169.

Trimble, "Successful fiber sensor for medical applications", May 1993, pp. 147-150, Proceedings SPIE vol. 1886.

(56) References Cited

OTHER PUBLICATIONS

Grossman et al, "Development of microbend sensors for pressure, load, displacement measurements in civil engineering", May 1994, pp. 112-125, Proceedings SPIE vol. 2191.
Lawrence et al, "Multi-parameter sensing with fiber bragg gratings", 1996, pp. 24-31, Proceedings of SPIE vol. 2872.
Schulz et al, "Health monitoring of adhesive joints using multi-axis fiber grating strain sensor system", Jan. 1999, pp. 41-52, Proceedings of SPIE vol. 3586.
"Fiber Optic Interferometer Fabry-Perot", http://physics-animations.com/sensors/English/interf.htm, pp. 1-5.
Katsuki et al, "The Experimental Research on the Health Monitoring of the Concrete Structures Using Optical Fiber Sensor", BAM International Symposium (NDT-CE 2003), Non-destructive Testing in Civil Engineering, Sep. 16-19, 2003.
Hayano et al., "Structural Health Monitoring System Using FBG Sensor Simultaneous Detection of Acceleration and Strain", Department of System Design Engineering, Keio University, pp. 1-10.
Ye et al., "A Polarization-maintaining Fiber Bragg Grating Interrogation System for Multi-Axis Strain Sensing", Measurement Science and Technology, Aug. 7, 2002, pp. 1446-1449.
Wippich et al., "Tunable Lasers and Fiber-Bragg-Grating Sensors", The Industrial Physicist, Jun./Jul. 2003, pp. 24-27.
Sorin, W.V. "Survey of Different Techniques", Optical Reflectometry for Component Characterization, Fiber Optic Test and Measurement, Dennis Derickson (editor), 1997, , Chapter 10, Section 10.5, pp. 424-429.
Schulz et al., "Advanced Fiber Grating Strain Sensor Systems for Bridges, Structures, and Highways", Proceedings of SPIE 3325, 212 (1998).
Schreiber et al., "Stress-induced Birefringence in Large-mode-area Micro-structured Optical Fibers", Optics Express, May 16, 2005, pp. 3637-3646, vol. 13 No. 10.
Xue et al., "Simultaneous Measurement of Stress and Temperature with a Fiber Bragg Grating Based on Loop Thin-Wall Section Beam", Mar. 2, 2006, pp. 1-16.
Soller et al., "High Resolution Optical Frequency Domain Reflectometry for Characterization of Components and Assemblies", Optics Express, Jan. 24, 2005, pp. 666-674, vol. 13 No. 2.
Satava, "How the Future of Surgery is Changing: Robotics, Telesurgery, Surgical Simulators and Other Advanced Technologies", May 2006, pp. 2-21.
Janssen et al., "Signal Averaging in the Undergraduate Laboratory", Europe Journal of Physics, 9 (1988), pp. 131-134.
Danisch et al., "Bend Enhanced Fiber Optic Sensors in a Teleoperation Application", Fiber Optic and Laser Sensors XI, 1993, pp. 73-85, SPIE vol. 2070.
Notification of the First Office Action as issued for Chinese Patent Application No. 200780009956.6, dated Feb. 5, 2010.
Notification of the Second Office Action as issued for Chinese Patent Application No. 200780009956.6, dated Dec. 14, 2010.
Matthew T. Raum, "Error Analysis of Three Dimensional Shape Sensing Algorithm", Virginia Tech, Apr. 26, 2005.
A. F. Abouraddy et al., "Towards multimaterial multifunctional fibres that see, hear, sense, and communicate", Nature Materials, vol. 6, Publication date: May 2007, pp. 336-347.
Sandra M. Klute et al., "Fiber-optic shape sensing and distributed strain measurements on a morphing chevron", 44th AIAA Aerospace Sciences Meeting and Exhibit, Conference dates: Jan. 9-12, 2006, pp. 1-23, Reno Nevada.
Roger R. Duncan et al., "Fiber-optic shape and position sensing", Proceedings of the 5th International Conference on Structural Health Monitoring (2005), Structural Health Monitoring, 2005: Advancements and Challenges for Implementation, Copyright 2005, p. 804-811.
Brooks A. Childers et al., "Recent development in the application of optical frequency domain reflectometry to distributed Bragg grating sensing", Luna Innovations and NASA Langley Research Center joint PowerPoint presentation.
Brooks A. Childers et al., "Recent development in the application of optical frequency domain reflectometry to distributed Bragg grating sensing", Fiber Optic Sensor Technology and Applications, pp. 19-31, Feb. 2002, Proc. SPIE vol. 4578.
Capouilliet et al., "A Fiber Bragg Grating Measurement System for Monitoring Optical Fiber Strain", IWCS/FOCUS Internat conference Nov. 12-15, 2001, pp. 240-248.
Kunzler et al., "Damage Evaluation and Analysis of Composite Pressure Vessels Using Fiber Bragg Gratings to Determine Structural Health", Proceedings of SPIE, vol. 5758, p. 168, 2005 (9 pages).
Udd et al., "Usage of Multi-Axis Fiber Grating Strain Sensors to Support Nondestructive Evaluation of Composite Parts and Adhesive Bond Lines", Structural Health Monitoring Workshop, Stanford University, p. 972, DEStech Publications, 2003 (9 pages).
Grobnic et al., "Localized High Birefringence Induced in SMF-28 Fiber by Femtosecond IR Laser Exposure of the Cladding", Journal of Lightwave Technology, vol. 25, No. 8, Aug. 2007, pp. 1996-2001.
Walker et al., "Shaping the radiation field of tilted fiber Bragg gratings", J. Opt. Soc. Am. B, vol. 22, No. 5, May 2005, pp. 962-975.
Ivanoff et al., "Tunable PDL of Twisted-Tilted Fiber Gratings", IEEE Photonics Technology Letters, vol. 15, No. 6, Jun. 2003, pp. 828-830.
Mihailov et al., "UV-induced polarization-dependent loss (PDL) in tilted fibre Bragg gratings: application of a PDL equaliser", IEE Proc.-Optoelectron., vol. 149, No. 5/6, Oct./Dec. 2002, pp. 211-216.
MacDonald, "Frequency domain optical reflectometer", May 15, 1981, Applied Optics, vol. 20, No. 10, pp. 1840-1844.
PCT International Search Report for PCT/US2007/064728, Applicant: Hansen Medical, Inc., Forms PCT/ISA210 and 220, dated Jul. 31, 2007 (7 pages).
PCT Written Opinion of the International Search Authority for PCT/US2007/064728, Applicant: Hansen Medical, Inc., Form PCT/ISA/237, dated Jul. 31, 2007 (9 pages).
Duncan et al., "Sensing Shape—Fiber-Bragg-Grating Sensor Arrays Monitor Shape at High Resolution", SPIES's OE Magazine, Sep. 2005, pp. 18-21 (4 pages).
Office Action from Related Application EP 08797926.6, Applicant: Hansen Medical, Inc., dated Jan. 17, 2011 (5 pages).
PCT International Search Report and Written Opinion of the International Searching Authority for PCT/US2008/073215, dated Jan. 21, 2009, Applicant: Hansen Medical, Inc., Forms PCT/ISA/210, 220 and 237 (15 pages).

* cited by examiner

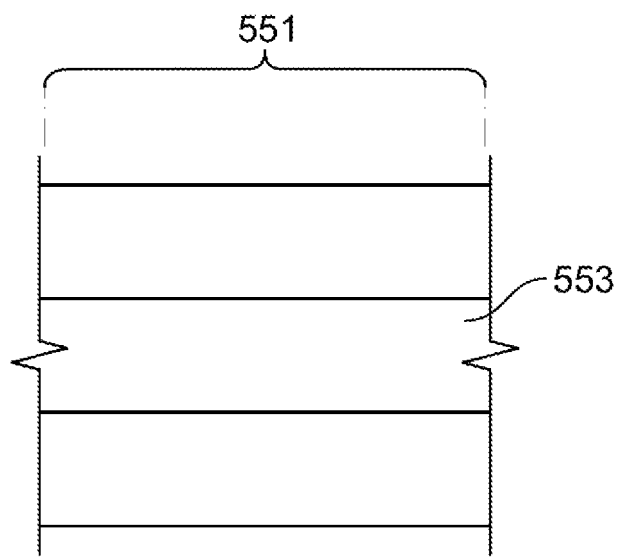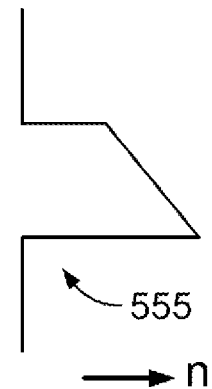
FIG. 8A    FIG. 8B
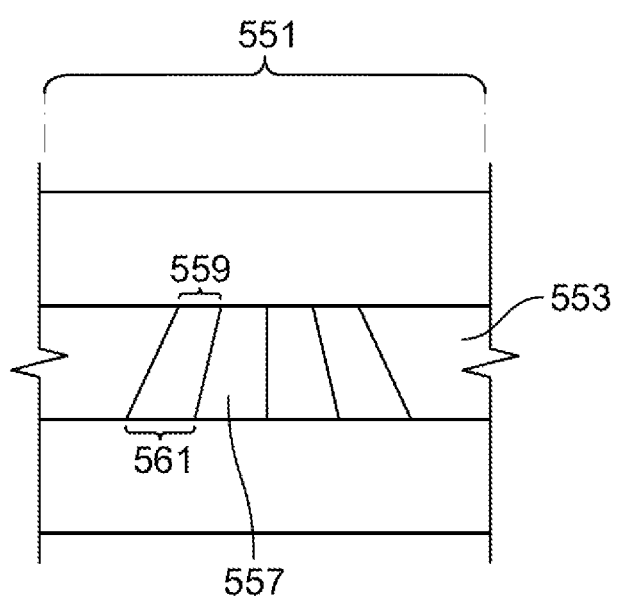
FIG. 8C

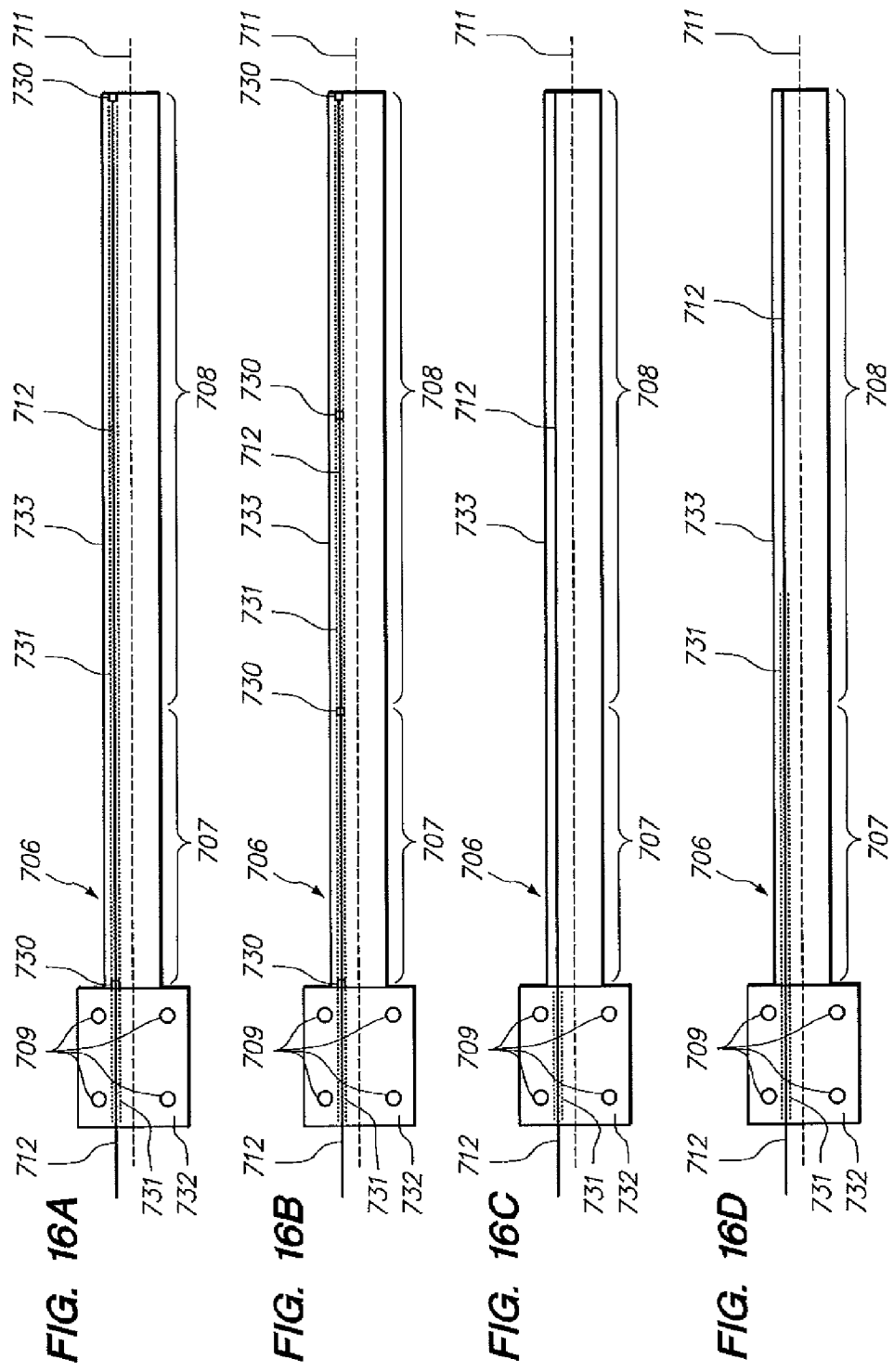

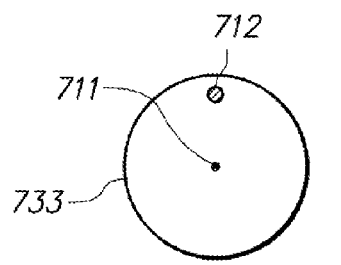
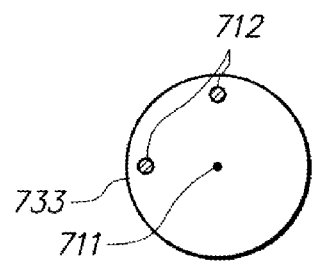
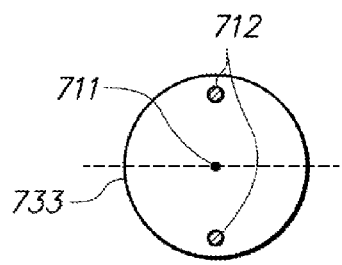
FIG. 24A    FIG. 24B    FIG. 24C
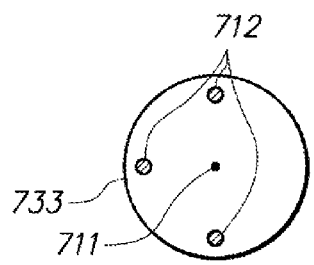
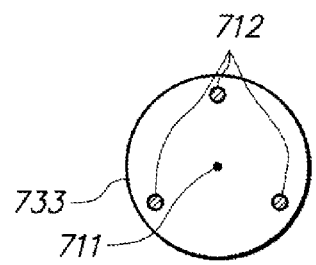
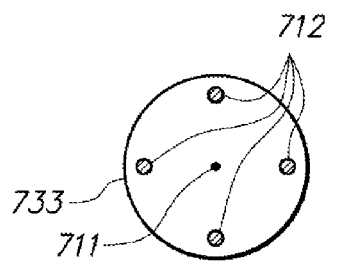
FIG. 24D    FIG. 24E    FIG. 24F
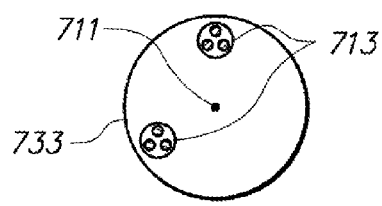
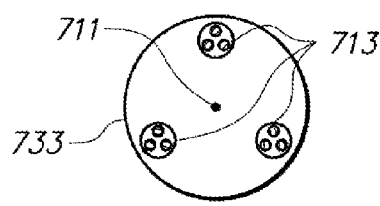
FIG. 24G    FIG. 24H

FIBER SHAPE SENSING SYSTEMS AND METHODS

CROSS-REFERENCE TO RELATED APPLICATION

This application claims the benefit of priority to U.S. Prov. Pat. App. 61/225,883 filed Jul. 15, 2009, which is incorporated herein by reference in its entirety.

BACKGROUND

Earlier efforts have demonstrated that three independent fiber lines containing multiplexed fiber gratings can be used to support shape sensing. This has been done by using three independent optical fibers in systems similar to those described by Chen, Bucholtz and others. Systems utilizing three independent fibers, in some instances, may by subject to the effects of spatial placement and relative motion between the optical fibers.

Multi-core optical fibers have also been utilized in certain systems. Multi-core optical fibers, however, may be subject to the need to break out the cores of the optical fibers for interfacing to read out units, and existing procedures for breaking out the fiber cores can be costly.

Thus, there is a need for improved systems utilizing fibers for shape sensing.

BRIEF SUMMARY

Variations of fiber shape sensing or measuring systems, devices and methods are described herein. In certain variations, systems may be suitable for the measurement of bend, strain, roll and/or twist in localized areas where three or more fibers, e.g., optical fibers, are tapered and/or bonded. In certain embodiments, the optical fibers may be tapered and/or bonded by being heated and drawn down over a sensing area or region of interest where the draw down is optionally stopped before significant cross coupling can occur. This allows for the creation of a small shape sensing region over which three or more optical fibers are uniformly bonded together. Fiber gratings may be written into this region to support bend or twist measurements.

In certain variations, at least one of the optical fibers of the three or more fibers which have been bonded together or one or more separate fibers may have one or more fiber gratings. The fiber gratings may have polarization dependence. In certain variations, one or more fiber grating(s) that have a tilt relative to the longitudinal axis of the optical fiber core may be written into at least one of the optical fibers. In certain embodiments, a fiber grating may be written into at least one of the optical fibers in such a way that the writing process results in birefringence of the fiber grating. Thus, when fibers having any of these types of fiber gratings are twisted, the change in the polarization state may be measured such that twist of the fibers may be measured.

In certain variations, a fiber optic shape sensing or measuring system may be capable of measuring bend angles, e.g., yaw and pitch, as well as twist or roll along the entire length or a portion of the length of the optical fiber, while using a single optical core. One or more fiber gratings or an array of fiber gratings may be written along an optical fiber, which may have a series of properties suitable for shape sensing. The properties of the optical fiber may include but are not limited to, a large optical core and an index of refraction gradient across the optical fiber, e.g., in the yaw and pitch directions. Optionally, the fiber can include birefringence along two orthogonal transverse directions, so that twist may be measured as well as yaw and pitch. In certain variations, the optical fiber may be a photonic crystal fiber which may have such shape sensing properties.

In certain variations, a shape sensing or measuring system may include a large core optical fiber. Yaw, pitch and/or twist for measuring shape may be measured by a combination of tilted fiber gratings and ordinary fiber gratings written across the core, with or without the need for an index of refraction gradient across the core.

One variation of a system may include three or more optical fibers. The fibers may have a bonded region to support strain transfer between the optical fibers and each of the optical fibers may have a fiber grating on each of the optical fibers along the bonded region.

Another variation of a system may include a large core optical fiber. A fiber grating may be written onto said optical fiber. A light source may be provided for illuminating the fiber grating and a spectral read out system may measure a property of a reflection of light from the fiber grating A variation of a system for measuring twist may include a light beam director, and an optical fiber having a first reference tilted fiber grating, a second tilted fiber grating and an end reflector. The system may include a polarizer and a spectrometer or spectral read out system. The light beam director may be configured to receive a light beam such that at least a portion of the light beam is directed from the light beam director into the optical fiber. The end reflector may be configured to reflect the light beam back through a tilted fiber grating to the light beam director, through a polarizer and onto a spectrometer or other spectral read out system to measure twist along the optical fiber at points associated with a tilted fiber grating.

A variation of a method for measuring twist along a fiber may include coupling a light beam into a light beam director and directing at least a portion of the light beam from the light beam director into an optical fiber. The optical fiber may have a first reference tilted fiber grating, a second tilted fiber grating and an end reflector. The method may include reflecting the light beam back through the tilted fiber gratings to the light beam director through a polarizer and onto a spectrometer or spectral read out system, and detecting a polarization state of a wavelength associated with a fiber grating to measure twist along a region of the fiber associated with the fiber grating.

Another variation of a system may include a light beam director, an optical fiber having a birefringent fiber grating, a polarizer, and a spectrometer or spectral read out system. The light beam director may be configured to receive a light beam such that at least a portion of the light beam is directed from the light beam director to the birefringent fiber grating of the optical fiber. The birefringent fiber grating can at least partially reflect the light beam back to the light beam director, through a polarizer and onto a spectrometer to measure twist along the optical fiber.

A variation of a method for measuring twist along a fiber may include coupling a light beam into a light beam director and directing at least a portion of the light beam from the light beam director into an optical fiber. The optical fiber may have a birefringent fiber grating. The method may include reflecting at least a portion of the light beam off of the birefringent fiber grating toward the light beam director, through a polarizer and onto a spectrometer or spectral read out system. A reflection spectra of the fiber grating is split into two distinct spectral peaks that are polarization dependent, and the relative amplitudes of the spectral peaks and change in their ratio is detected to measure twist along the fiber.

Another variation of a system may include an optical fiber having a birefringent axes. A first fiber grating may be written on the optical fiber such that two effective fiber gratings are established one on each of the birefringent axes, which allow for the measurement of bend.

In certain variations, the fiber systems described herein may be utilized or incorporated along an axis of a manual or robotically controlled elongate member or instrument of a surgical system or other medical device or instrument for sensing or measuring the shape, position, twist, roll, deflection, displacement or bend of the elongate member in a patient's body.

BRIEF DESCRIPTION OF THE SEVERAL VIEWS OF THE DRAWINGS

The drawings constitute a part of this specification and include exemplary embodiments, which may be embodied in various forms. It is to be understood that in some instances various aspects of the embodiments may be shown exaggerated or enlarged to facilitate an understanding of the embodiments.

FIG. 8A is a magnified side view of a photonic crystal fiber having a linear index of refraction gradient across the core.

FIG. 8B is a graphical diagram of the index of refraction for the fiber of FIG. 8A.

FIG. 8C is a magnified side view of a variation of a photonic crystal fiber and a fiber grating written into it.

FIGS. 16A-16D illustrate implementations of an optical fiber with a grating to an elongate instrument such as a robotically-steerable catheter.

FIGS. 24A-24H illustrate cross sectional views of elongate instruments with various fiber positions and configurations.

DETAILED DESCRIPTION

Variations of the devices are best understood from the detailed description when read in conjunction with the accompanying drawings. It is emphasized that, according to common practice, the various features of the drawings may not be to-scale. On the contrary, the dimensions of the various features may be arbitrarily expanded or reduced for clarity. The drawings are taken for illustrative purposes only and are not intended to define or limit the scope of the claims to that which is shown.

Figure 1A:
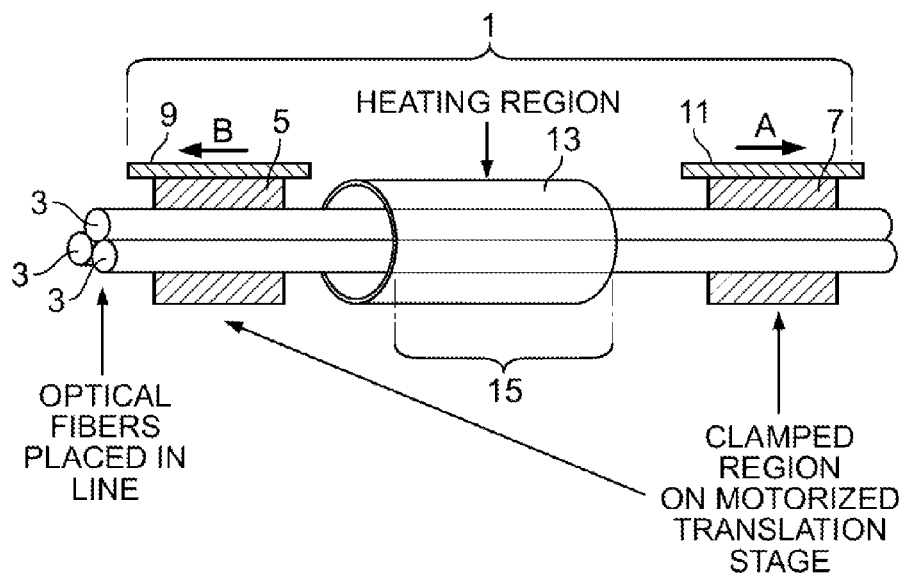
FIG. 1A is a perspective view of a method to fabricate a shape sensing or measuring system.
Figure 1B:
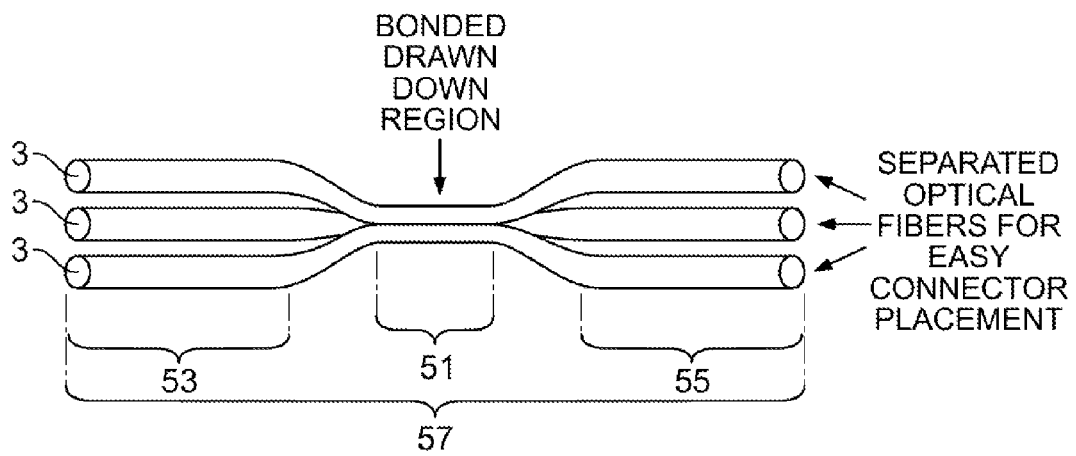
FIG. 1B is a side view of the shape sensing system of FIG. 1, including a bonded region.

FIG. 1B illustrates one variation of a shape sensing or measuring system 57 having three aligned fibers, e.g., optical fibers 3. The system includes a combined, adhered, fused or bonded region 51. The system may also include end regions 53 and 55 where the optical fibers 3 are mechanically independent and may be easily interfaced to connectors or spliced. In certain variations, the bonded region 51 may be designed such that when light is coupled into any one of the optical fibers 3 there is virtually no or substantially no cross coupling in the bonded region 51 to any other of the optical fibers 3. Thus the region 51 may allow for good strain transfer between the optical fibers 3 with minimal or virtually no cross coupling. In certain variations, one or more fiber gratings can be written onto the optical fibers. Examples of fiber gratings include, but are not limited to: Bragg fiber gratings, and long period fiber gratings. Various Bragg fiber gratings may be utilized, including, for example, those with (1) uniform period, (2) apodized fiber gratings designed for spectral shape and/or (3) chirped fiber gratings that have a non-uniform period and are designed to reflect a broad wavelength spectrum.

FIG. 1A illustrates one variation of a process or mechanism 1 for bonding multiple fibers together such that good strain transfer may be obtained between the fibers. The process or mechanism 1 may be utilized to produce the shape sensing system 57 illustrated in FIG. 1B. Clamps 5 and 7 are used to hold the three optical fibers 3 in place and to place them under tension via mechanical stages 9 and 11 (e.g., motorized translation stages), which can exert a controllable force on the clamped optical fibers 3 in the directions indicated by arrows A & B. A heater 13, or other temperature altering device or substance may be used to increase the temperature substantially uniformly on a region 15 of the clamped optical fibers 3. This allows the optical fibers 3 to soften such that they may be pulled, drawn or reduced down in diameter. The heater 13 may be, e.g., a butane flame arrangement or a metallic tube that is resistively heated, or any other device suitable for controllably heating or raising the temperature of the optical fibers.

By controlling a drawing force exerted by mechanical stages 9 and 11 and increasing the temperature of region 15 of the optical fibers 3, the optical fibers 3 will soften and may be drawn down together. This in turn establishes a region where the optical fibers 3 are physically bonded. The bonded region may be tapered. Various types of optical fibers 3 may be utilized, including, for example, quartz optical fibers, sapphire optical fiber and optical fiber composed of other crystalline materials. When utilizing quartz optical fibers, the bonded region will include an area where the quartz surface of the optical fibers has melted, and upon cooling, solidified to form a quartz bond region.

In certain variations, procedures for processing the optical fibers 3 illustrated in FIGS. 1A and 1B may be similar to those employed with biconical fused 2 by 2 and 3 by 3 couplers, which are established by commercial vendors such as Amphenol and Gould Fiber Optics. However, unlike conventional fiber coupler technology, the surfaces of the optical fibers 3 are bonded for strain transfer between the optical fibers 3. As a result, the tapers associated with the bonded region 51 of optical fibers 3 may be less severe than those created using conventional fiber coupler technology and the shape sensing or measuring system 57 may be mechanically more robust. Optionally, the bonded region of the fibers may be fused in a manner similar to that used to form fused biconical couplers in the telecommunication industry.

Figure 2:
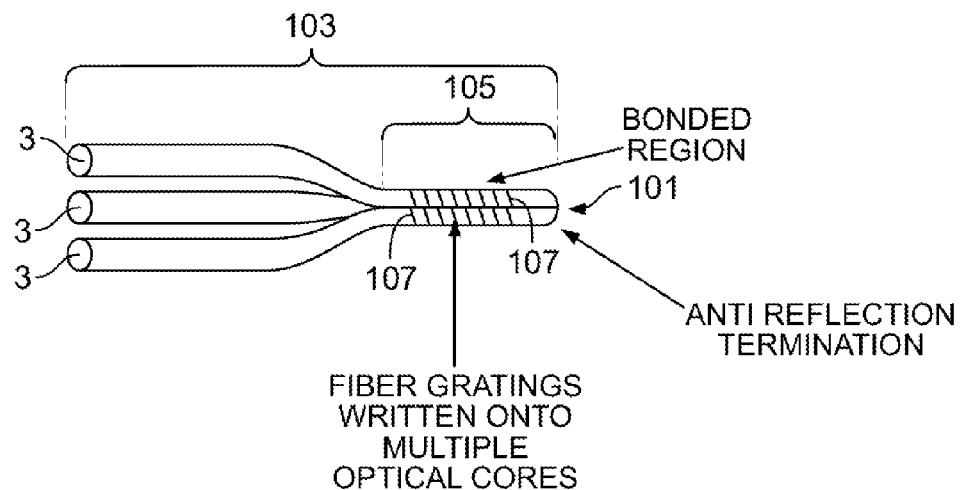
FIG. 2 is a perspective view of a variation of a shape sensing or measuring system including an antireflection end.

Referring to FIG. 2, in another variation, the shape sensing or measuring system 57 of FIG. 1B may be cleaved approximately in the center of bonded region 51, creating cleaved shape sensing or measuring system 103. The end 101 of the cleaved system 103 may be processed to minimize back reflection. For example, this may be accomplished by forming a spherical end at end 101 or by adding an antireflection coating to end 101 or by forming an angled cleave. Optionally, one or more fiber gratings 107 may be written onto the optical fibers 3 of system 103 in bonded region 105, thereby enabling the measurement of bend in two orthogonal directions or twist or roll along the length of bonded region 105. The fiber gratings may be written onto the cores of the optical fibers.

The cleaved system 103 may be useful for a variety of applications. For example, for applications involving robotically or manually controlled medical catheters, where it is desirable to minimize the overall size of the catheter, particularly at the distal end. The cleaved system 103 can reduce the overall cost of a shape sensing system, which is important for applications involving disposable components, e.g., disposable catheters. The cleaved system 103 may also be useful to create a shape sensing system that allows for a single ended read out system.

The systems associated with FIGS. 1 and 2 may include polarization preserving or maintaining optical fiber when it is desirable to be able to define and control the polarization state of light propagating through the system. For example, optical frequency domain reflectometer systems that require polarization control to operate effectively may include polarization preserving optical fiber. A number of different types of polarization preserving optical fiber may be utilized. One example is elliptical core optical fiber, that may be made with one or more flat sides. This may be done by machining flats onto the side of the perform and then drawing an optical fiber with the same geometry. The flat provides a reference to orientation. An example of this type of fiber is D shaped optical fiber, originally developed and sold commercially by Andrew Corporation. The flat side feature of these fibers allows the polarization preserving fibers to be fabricated with sides angled such that the fibers may be placed and drawn with specific desirable orientations to optimize shape sensing capabilities.

Figure 3:
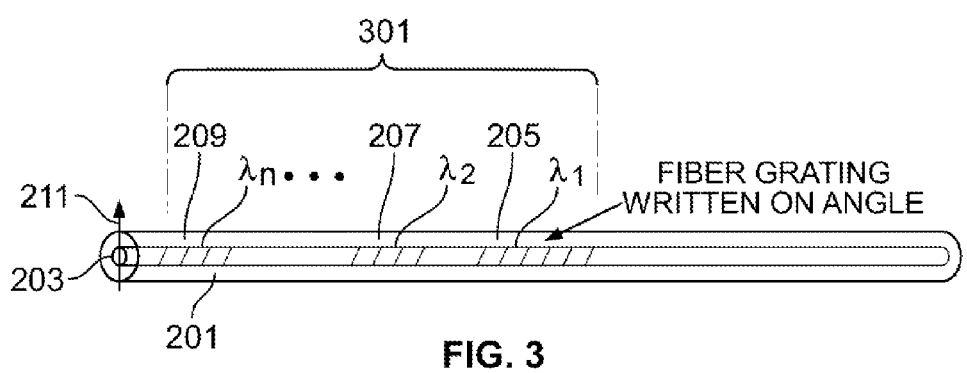
FIG. 3 is a perspective view of a twist measurement system to support a shape sensing.

FIG. 3 illustrates an example of a shape sensing system which allows for the measurement of twist or roll by measuring changes in the polarization state of reflected light from regions along the axis of a probe. Such a system may allow for shape sensing for small diameter probes (among other applications) where twist may be measured along the axis of the probe. The system includes an optical fiber 201 with a light guiding core 203 having a series of tilted fiber gratings 205, 207 and 209 written along the core 203. One or more optical fibers may be utilized in the system. Optionally, the optical fibers may be bonded together as described above according to the systems of FIGS. 1-2. The fiber gratings 205, 207 and 209 may be tilted so that they are polarization sensitive or have a polarization dependence corresponding to the direction of tilt. The direction of tilt can vary. In this particular variation, the direction of tilt is along the axis 211. Each of the fiber gratings 205, 207 and 209 may be written at a different wavelength so that multiple fiber gratings may be interrogated using standard wavelength division multiplexing techniques. Optionally, each of the successive tilted fiber gratings 205, 207, 209 may be written at the same wavelength with low reflectivity or optionally two or more of the fiber gratings may be written at the same wavelength. These fiber gratings may be interrogated using well known standard optical frequency domain reflectometry techniques developed by NASA. The tilted fiber gratings 205, 207 and 209 according to any of the above described variations indicate an array 301 of n fiber gratings representing n points along the optical fiber 201 where twist may be measured.

Figure 4:
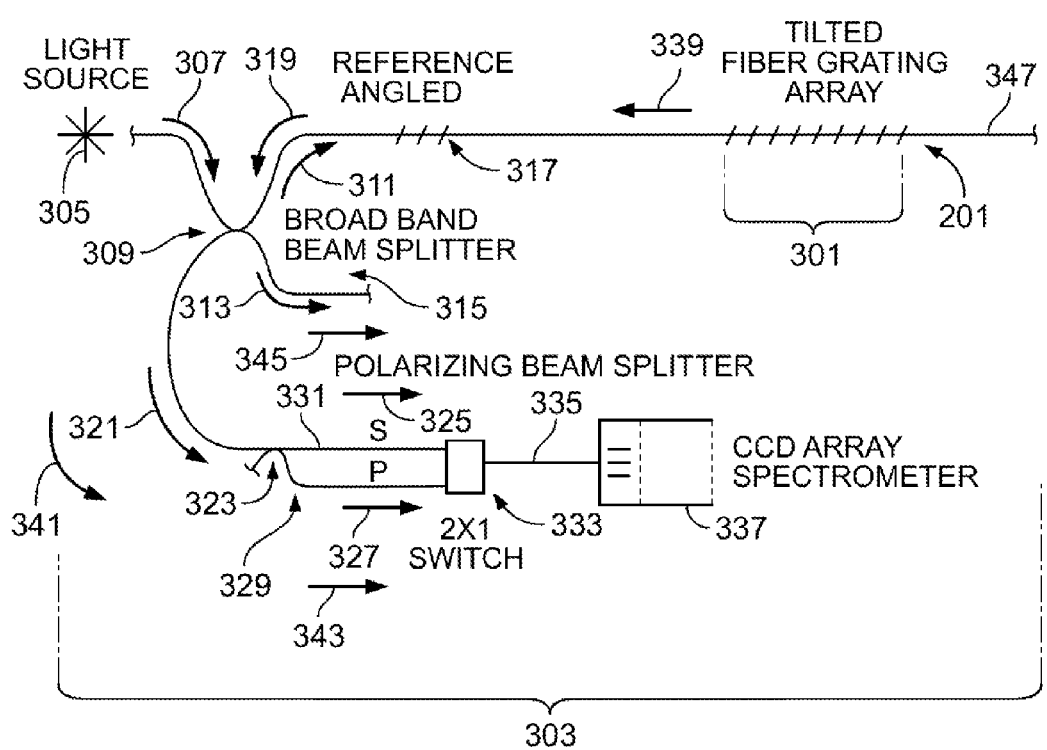
FIG. 4 is a perspective view of a variation of a twist measurement system for shape sensing or measuring utilizing a CCD array spectrometer.

FIG. 4 illustrates one variation of a shape sensing or measuring system 303 that can measure twist or roll. The system 303 may measure twist along an optical fiber 201 at points associated with the tilted fiber grating array 301. A light source 305 is provided, e.g., an optically spectrally broad band light source. The light source 305 couples a beam of light 307 into a spectrally broadband 2 by 2 coupler 309. A variety of broadband couplers known by persons having ordinary skill in the art may be used including, e.g., a fused biconical taper coupler. The coupler 309 splits the light beam 307 into the light beam 313 that is directed to the terminating end 315, which directs light beam 313 out of the system 303, while minimizing back reflection.

The coupler 309 also splits the light beam 307 into the light beam 311 which is directed into the optical fiber 201 and the light beam 311 can reach a reference tilted fiber grating 317 that is positioned in a location where the twist of the optical fiber 201 is known. A portion 319 of the light beam 311 is reflected by the tilted reference fiber grating 317 along the optical fiber 201 to the coupler 309. The portion of light beam 319 is directed as the light beam 321 to the polarizing beamsplitter 323, which splits the light beam 321 into the orthogonal s and p polarization components (light beams 325 and 327 respectively) via the fiber lines 331 and 329 respectively. The light beams 325 and 327 reach the 2 by 1 optical switch 333, which may alternately direct the light beams 325 and 327 onto a CCD array spectrometer 337 (or reflectometer or detector or other instrument for measuring light or the properties of light or other spectral read out system). The CCD array spectrometer 337 detects the relative amount of light in the s and p polarization state such that the twist orientation of the reference fiber grating 317 may be determined.

The light beam 311, after passing the reference fiber grating 317, can reach the tilted fiber grating array 301, which includes a series of n fiber gratings that may optionally be wavelength division multiplexed. The reflection, in the form of light beam 339, from the fiber grating array 301 is directed back to the coupler 309. A portion of the light beam 339 is directed as light beam 341 to the polarizing beamsplitter 323, and light beam 341 is split into s and p polarization states as the light beams 345 and 343 respectively, in the fiber lines 331 and 329 respectively. The light beams 343 and 345 are directed into the 2 by 1 switch 333 which in turn alternates these two light beams onto the CCD array spectrometer 337 so that the degree of polarization for each wavelength associated with the fiber gratings of the fiber grating array 301 may be assessed allowing the degree of twist along the region of the fiber 201 associated with the fiber grating array 301 to be measured.

The system of FIG. 4 can be operated with or include tilted fiber gratings that may have a variety of different optical reflection and transmission characteristics.

Figure 4A:
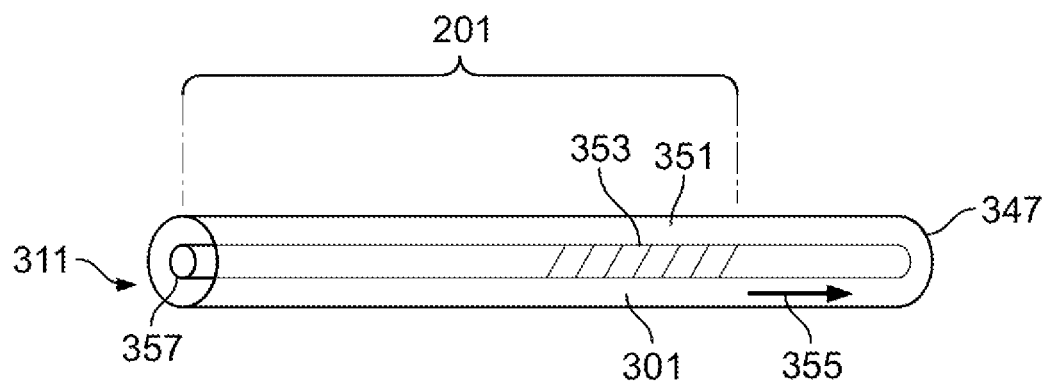
FIG. 4A is a view of an angled fiber grating written into optical fiber.

FIG. 4a illustrates a variation of a shape sensing system including an optical fiber 201, which has fiber gratings 301 that are tilted at a large angle relative to the longitudinal axis of the fiber 201. A large angle may be about 10 degrees or greater or range from about 10 to over 80 degrees with a 45 degree angle being typical. Where an optical fiber having such fiber gratings is utilized in a shape sensing system as described above with reference to FIG. 4, the light beam 311 may have a component 353 that is largely directed into the cladding 351 of the optical fiber 201. The light beam component 353 may have a preferred polarization state because of the steep angle (relative to the longitudinal axis of the optical fiber) associated with the tilted fiber gratings 301. The degree to which the light is polarized depends upon the angle of the tilt of the fiber grating. The light beam 311 may have a second component 355 and the second component 355 may be guided by the core 357 of the optical fiber 201. The component 357 may be partially polarized through the action of the tilted fiber gratings 301 and may propagate to the end 347 of the optical fiber 201. In order for a portion of the light beam component 355 to return to the CCD array spectrometer provisions may be included in the system so that the light beam 355 may reflect back.

Figure 4B:
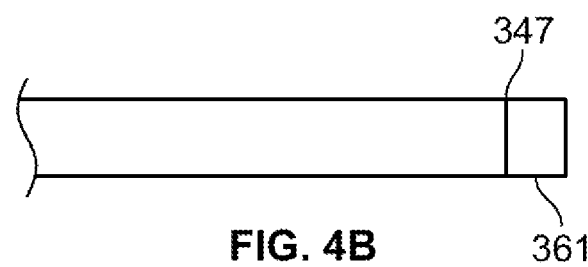
FIG. 4B shows an optical fiber with a reflecting end.

For example, FIG. 4b shows the fiber end 347 of optical fiber 201 having a reflector 361 connected thereto. A variety of reflector components, materials or substances may be utilized. For example, the reflector 361 can be a metallic coating that may be aluminum, silver, or gold or made from other reflective materials. The reflector 361 may be a single or multiple layer dielectric coating. The reflector 361 coat may be obtained by using polishing or cleaving techniques to create a flat end 347 and/or having the end terminate in a region having a different or significantly different index of refraction from that of the optical fiber, such as, for example, air or a high index liquid or fluid.

Figure 4C:
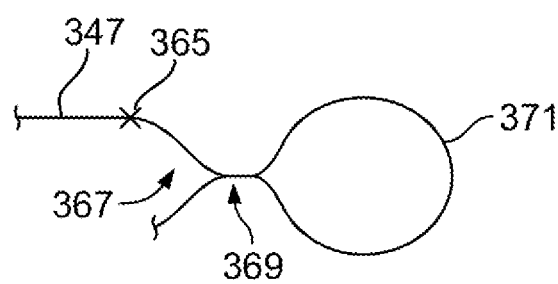
FIG. 4C shows a beamsplitter and fiber loop acting as an end reflector.
Figure 4D:
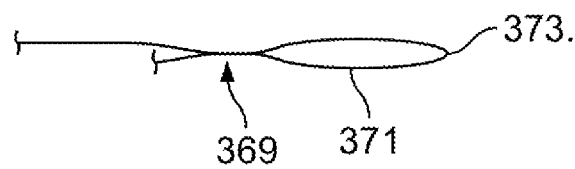
FIG. 4D illustrates a reflecting end similar to FIG. 4C using a tight bend to minimize overall diameter.

Referring to FIG. 4c, another method for directing a portion of the light beam 355 back into the system, e.g., toward a CCD array spectrometer, involves connecting the fiber end 347 via a splice 365 to a first end 367 of a coupler 369. Second and third ends of the coupler 369 may form a loop 371 that directs back to the coupler 369, and may direct a portion of the light beam 355 back into the optical fiber 201. Optionally, as shown in FIG. 4d, a portion 373 of the loop 371 may be bent very sharply using techniques that are available commercially from companies such as Amphenol. The tight bend 373 allows for a compact package. Such a configuration may be required or suitable for use in applications such as manually or robotically controlled catheters where it may be desirable for the overall diameters of the system to be minimized.

Figure 5:
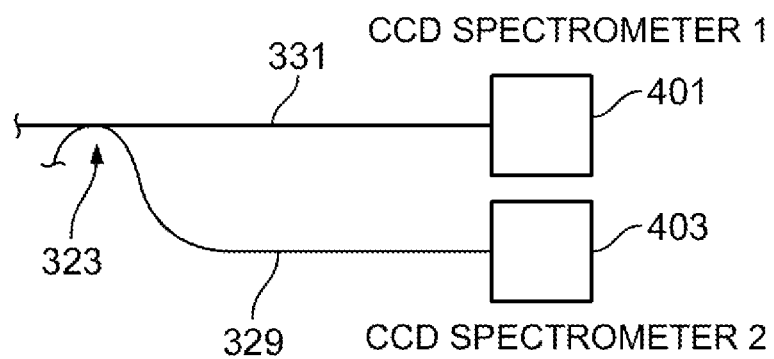
FIG. 5 is a perspective view of a variation of a shape sensing or measuring system utilizing two separate CCD spectrometers.

FIG. 5 shows an alternate variation of the shape sensing or measuring system of FIG. 4 which can measure twist. Two separate CCD spectrometers are provided. Spectrometer 401 may be used to monitor the light beam signals from the optical fiber 331 and the spectrometer 403 may be used to monitor the light beam signals from the optical fiber 329. These two separate CCD spectrometers may be used in place of the 2 by 1 switch 333 and the single CCD spectrometer 337 (illustrated in FIG. 4), while performing a similar function.

An advantage of the variation illustrated in FIG. 5 which utilizes two separate spectrometers is that the s and p polarization states of the tilted fiber gratings may be monitored continuously with no or minimal loss of signal due to the switching operation. An advantage of the variation illustrated in FIG. 4, however, is that a single CCD spectrometer is used for monitoring the light signals, thereby minimizing or eliminating the possibility of relative drift that may occur in the response of multiple CCD spectrometers. Such a drift could result in an error in measuring the degree of polarization and the twist. The use of a single CCD spectrometer may also be more cost effective, as CCD spectrometers in general may be more expensive than a 2 by 1 switch. A spectrometer or reflectometer or detector or other spectral read out system may be used in the variations described herein.

Figure 6:
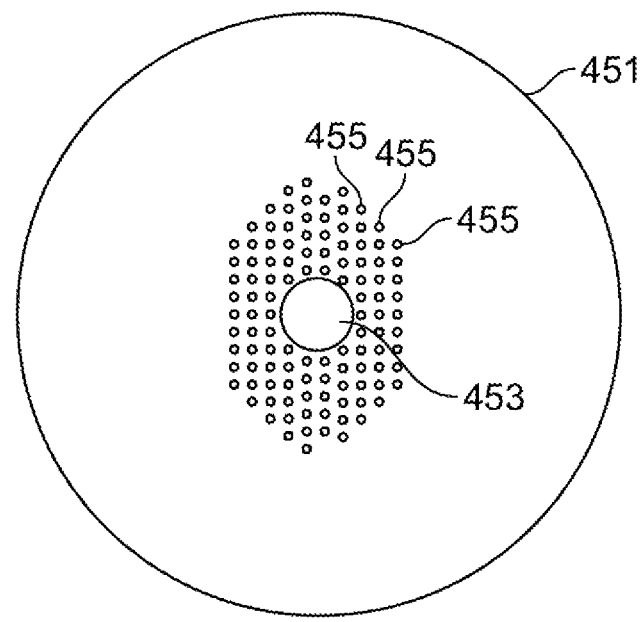
FIG. 6 is an end view of a variation of a photonic crystal fiber.

In certain variations, a shape sensing or measuring system may include one or more large core optical fibers. Optionally, two or more large core optical fibers may be bonded together as described above according to the systems of FIGS. 1-2 or a single large core optical fiber may be utilized. FIG. 6 shows an end view of a photonic crystal fiber (PCF) 451, which is one example of a large core optical fiber. A photonic crystal fiber 451 may include a core area 453 that may be larger or significantly larger than a conventional single mode fiber. The PCF 451 may also include a cladding structure that may consist of arrays of air holes 455 which can result in large mode field diameters. Crystal Fibres A/S of Birkerod, Denmark offers commercial photonic crystal fibers of this type having core diameters of up to 35 microns (LMA-35) that allow single mode operation at telecom wavelengths associated with conventional single mode optical fiber. In the PCF 451, the separation between the outer opposite edges of the fiber core 453 diameter may be large enough such that when the fiber 451 is bent, there is a significant strain difference between the opposite edges or positions across the fiber core 453. The strain differences may allow various shape measurements of the fiber 451 to be made. Large core optical fibers may vary in size. For example a large core optical fiber may have a diameter greater than or equal to about 10 microns or greater than or equal to about 20 microns. Optionally, the large core optical fiber may be greater than 20 microns or may be 30 or 40 microns.

Figure 7A:
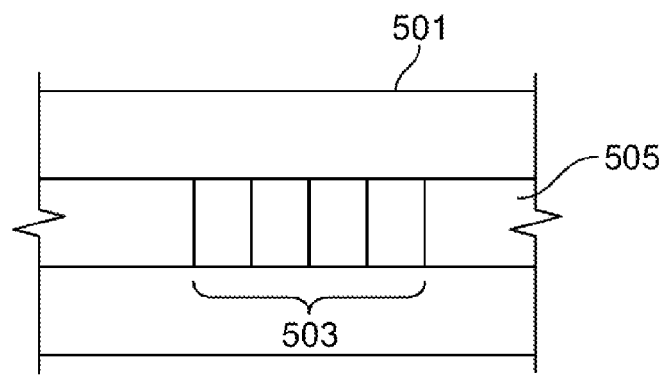
FIG. 7A is a magnified side view of a photonic crystal fiber with a fiber grating written into its large core.

FIG. 7A shows a side view of one variation of a single photonic crystal fiber (PCF) 501 in a substantially straight configuration. A fiber grating 503 is written across the core 505 of the PCF 501. When the fiber grating 503 is illuminated by a broadband light source the reflected light beam from the fiber grating 503 may have a spectral profile wavelength/intensity curve similar to 507 (shown in the graph of FIG. 7C).

Figure 7B:
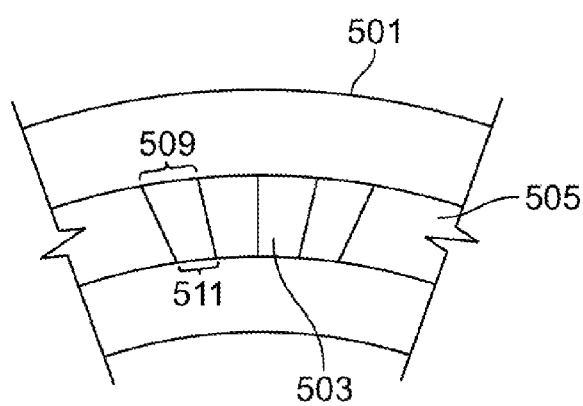
FIG. 7B is a magnified side view of a photonic crystal fiber and fiber grating of FIG. 7A shown in a bent configuration.
Figure 7C:
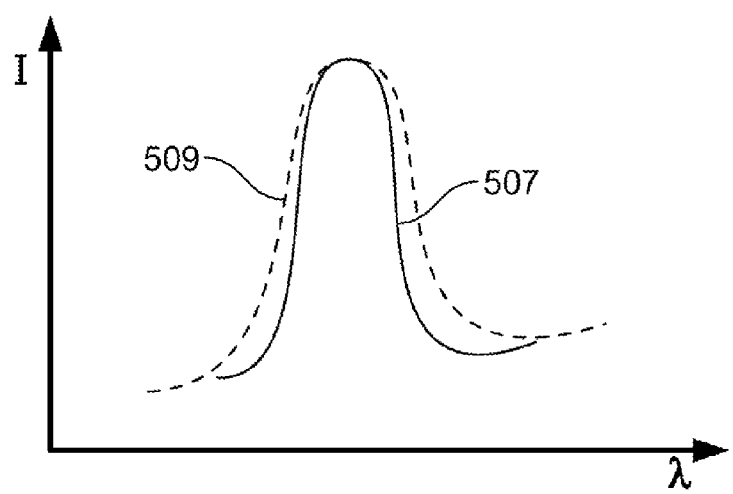
FIG. 7C is a line graph showing the spectral profiles for light reflected from the fiber gratings of FIGS. 7A and 7B.

FIG. 7B shows the PCF 501 bent into a curved position such that the period 509 of the fiber grating 503 on the tension side of the fiber core 505 is longer than the period 511 of the fiber grating 503 on the compression side of the fiber core 505. As a result, the effective period of the fiber grating 503 will vary across the core and when the fiber grating is illuminated in this state by a broadband light beam the spectral profile 509 reflected from the fiber grating will be broadened. By measuring this broadening or the width or change of the spectral profile, the bending of the fiber may be measured.

Because this represents a spectral measurement, issues associated with amplitude changes in the measurement system may be avoided. The shape sensing or measuring system illustrated in FIGS. 7A-7C can measure bending and optionally it may indicate the direction of bend. Additional refinements may be made such that the system can indicate the direction of bend.

FIG. 8A shows a side view of one variation of a PCF 551 having a large core 553 that has a linear index of refraction gradient across the core. As shown in the graphical diagram 555 in FIG. 8B, the index of refraction varies from a lower value at the diametric top to a higher value at the diametric bottom, where the index of refraction may increase in the direction of arrow n. FIG. 8B shows the index of refraction increasing across the core 553 of the fiber 551, where the index of refraction is low at the top of the core and higher at the bottom of the core.

As shown in FIG. 8C, a fiber grating 557 may be written onto the PCF 551 and may have an effective period 559 near the diametric top of the core 553 (e.g., where an index of refraction is low) that is substantially shorter than the effective period 561 near the diametric bottom of the core 553 (e.g., where the index of refraction is higher).

Comparing PCF 551 of FIG. 8C with fiber 501 of FIG. 7B, it is apparent that the fiber grating 557 of FIG. 8C will have a broadened spectral profile, similar to fiber grating 503 of optical fiber 501 when the optical fiber 501 is bent. These configurations or methods effectively allow the spectral profile to be "biased" so that the direction of bend of the fiber may be determined. That is one side of the optical fiber core has a grating written into it that has a shorter period near one side than the other. When the fiber is bent it will elongate or shorten the period of the grating depending on the direction of bend. This in turn will change the overall spectral profile from its initial biased state where the period varies across the core. As an example, the linear index of refraction across the core could be designed so that when the fiber 551 is straight it will have a spectral profile corresponding to a bend diameter of 10 mm. The shift of the spectral profile effectively provides a "bias". That is when the fiber is bent in a direction along the axis of the refractive index gradient across the core 557 the spectral shift is distinct from an equal bend in the opposite direction. This effect is also illustrated in FIG. 9 below.

Figure 9A:
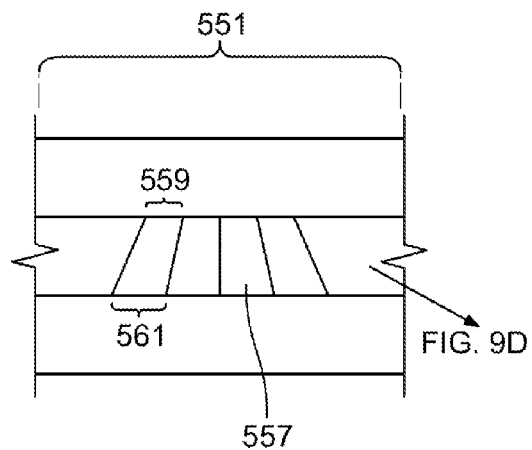
FIG. 9A is a magnified side view of a photonic crystal fiber with a linear index of refraction gradient across the core and a fiber grating written into it.

Referring to FIG. 9A, when PCF 551 is substantially straight, the period 559 at the top of the core 557 and the period 561 at the bottom of the core 557 may have a configuration as shown in FIG. 8B. When PCF 551 is illuminated by a broad band light beam, this results in a reflected wavelength/intensity spectral profile 601 (shown in FIG. 9D).

Figure 9B:
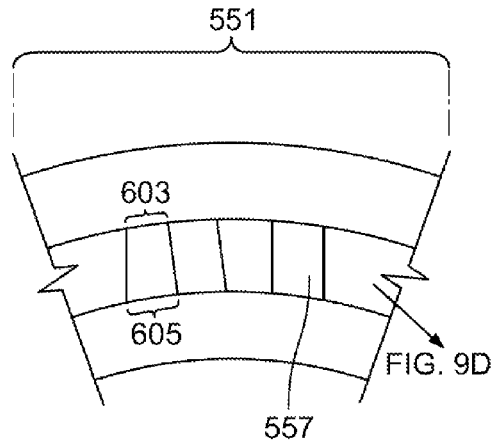
FIG. 9B is a magnified side view of a photonic crystal fiber and fiber grating as in FIG. 9A shown in a bent configuration.

Referring to FIG. 9B, when PCF 551 is bent so that the diametric top of the core 557 is under tension, the period 603 associated with the top of the fiber grating is moved to a longer period, compared to 559, and the bottom period 605 is moved toward a shorter period, compared to that of 561, due to compression. This results in the wavelength/intensity spectral profile 607 (shown in FIG. 9D) being narrower at its full width half maximum value in comparison to the spectral profile 601.

Figure 9C:
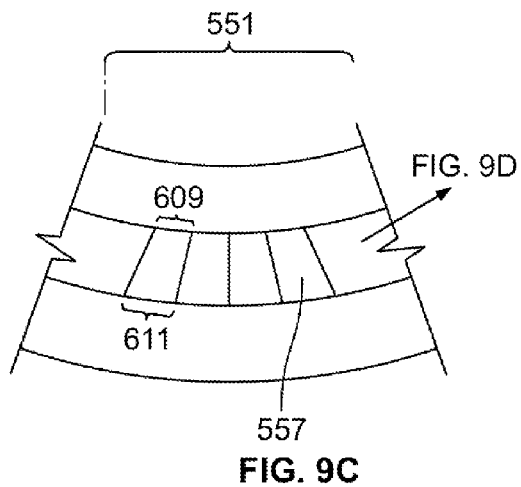
FIG. 9C is a magnified side view of a photonic crystal fiber and fiber grating as in FIG. 9A shown in a bent configuration.
Figure 9D:
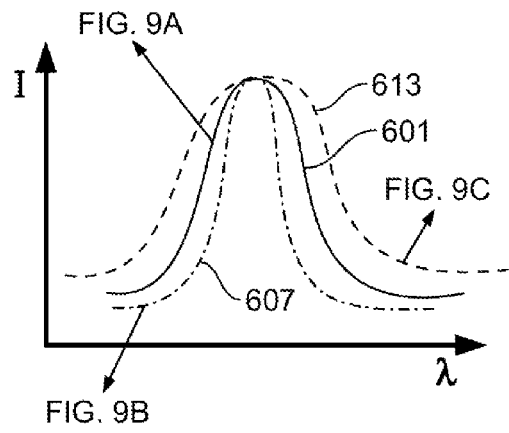
FIG. 9D is a line graph showing the spectral profiles for light reflected from the fibers of FIGS. 9A-9C.

Referring to FIG. 9C, when the PCF 551 is bent so that the top of the core 557 is under compression, the period 609 becomes shorter than the period 559 and the period 611 becomes longer than the period 561. The spectral profile 613 (shown in FIG. 9D) associated with the fiber grating 557 in this condition is broadened at its full width half maximum in comparison to the spectral profile 601.

Variations of mechanisms or processes for inducing or creating a refractive index gradient in the core of various optical fibers, such as a PCF, are provided. The first mechanism involves the use of ultraviolet light in a manner similar to that used in the fabrication of fiber gratings. For example, exposure of a germanium doped core to ultraviolet light at the appropriate wavelength may result in an increase in the index of refraction of the core. The appropriate wavelength may be about 240 nm which is commonly used or a series of other wavelengths that are described in the literature. Also, by adjusting the ultraviolet or other light exposure intensity and time across the core, the index of refraction profile may be adjusted.

Another mechanism for inducing or creating a refractive index includes adjusting the position and/or concentration of dopant material, such as germanium, during the fabrication process associated with making an optical fiber. In another mechanism, the geometry and position of holes in the optical fiber may be adjusted.

In certain variations, a shape sensing or measuring system may have two dimensional bend sensor capabilities. The capabilities may be provided by adding additional features to a PCF. For example, holes may be added to a PCF fiber to make it birefringent and/or polarization preserving.

In the above variations according to FIGS. 6-9, a large core optical could include a tilted or birefringent fiber grating to support or allow for the measurement of twist.

Figure 10:
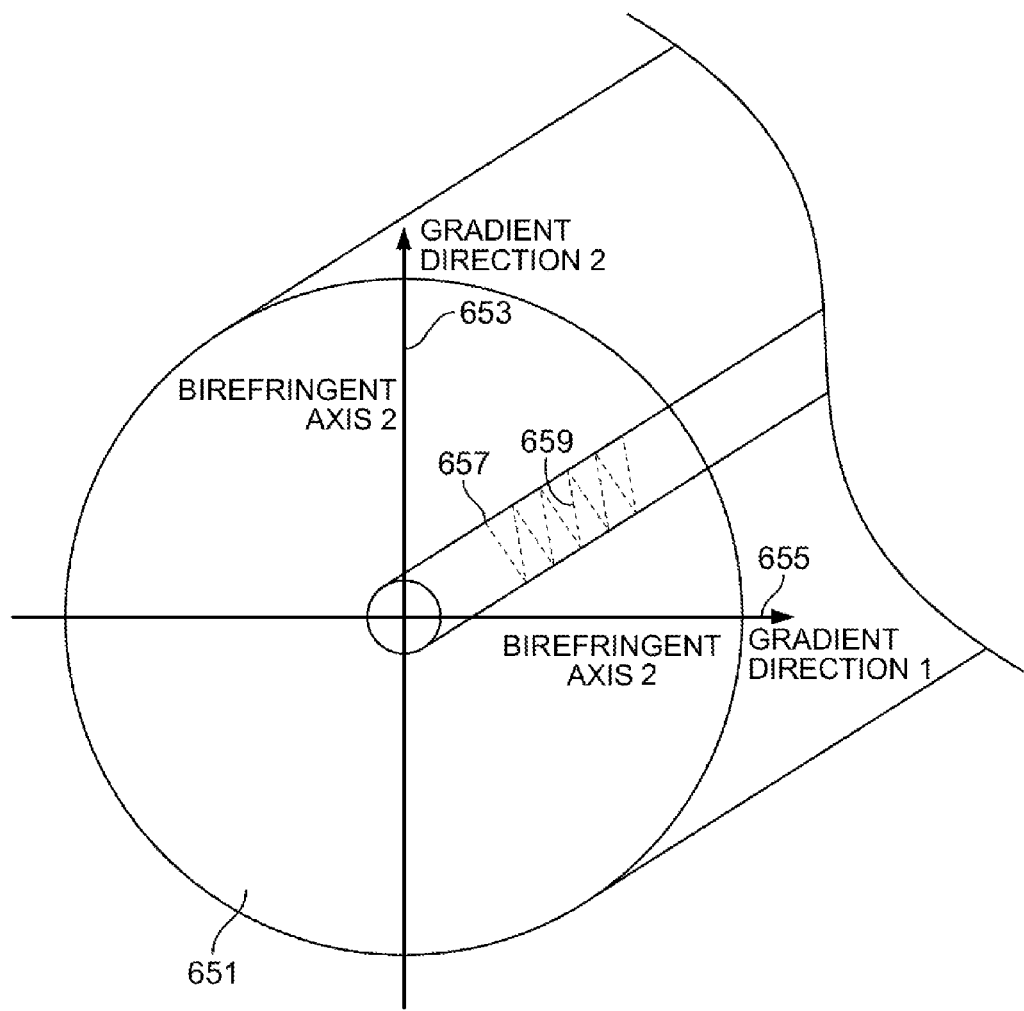
FIG. 10 is a cross sectional magnified perspective view of a variation of a shape sensing system including birefringent axes.

Referring to FIG. 10, another variation of a shape sensing or measuring system includes an optical fiber having birefringent axes 653 and 655. Along each of the axes 653 and 655 an index of refraction variation or gradient may be established that may be linear, similar to that shown in FIG. 8. When a fiber grating 657 is written onto this type of optical fiber, two effective fiber gratings may be established along each of the birefringent axes 653 and 655. The two effective fiber gratings can be used to measure yaw and pitch along the two orthogonal axes by the methods described in association with FIGS. 7-9. Optionally the fiber gratings may be used to measure twist or roll along the fiber or axes.

The fiber gratings may be interrogated independently by separating out the two polarization states onto a fiber grating read out unit. Such read out units may be similar to or include, for example, those used by E. Udd to support fiber grating damage assessment systems as described in: M, Kunzler, E. Udd, S. Kreger, M. Johnson and V. Henrie, "Damage Evaluation and Analysis of Composite Pressure Vessels Using Fiber Bragg Gratings to Determine Structural Health", Proceedings of SPIE, Vol. 5758, p. 168, 2005; and E. Udd et al, "Usage of Multi-Axis Fiber Grating Strain Sensors to Support Nondestructive Evaluation of Composite Parts and Adhesive Bond Lines", Structural Health Monitoring Workshop, Stanford University, DEStech Publications, p. 972, 2003. These references are incorporated herein by reference in their entirety for all purposes.

In certain variations, a fiber grating or second fiber grating 659 may be written at an angle at a wavelength that is different from that associated with fiber grating 657 in order to establish or measure twist of the fiber. The orientation of the tilted fiber grating 659 could be controlled relative to the birefringent axes. For example, the tilted fiber grating 659 may be written along an axis that is between the birefringent axes. By controlling wavelength, tilt and/or orientation of the second fiber grating 659 relative to the birefringent axes, it may be possible to generate enough of a polarization signal such that twist along the axis of an optical fiber, such as a PCF fiber, may be established or measured.

Figure 11:
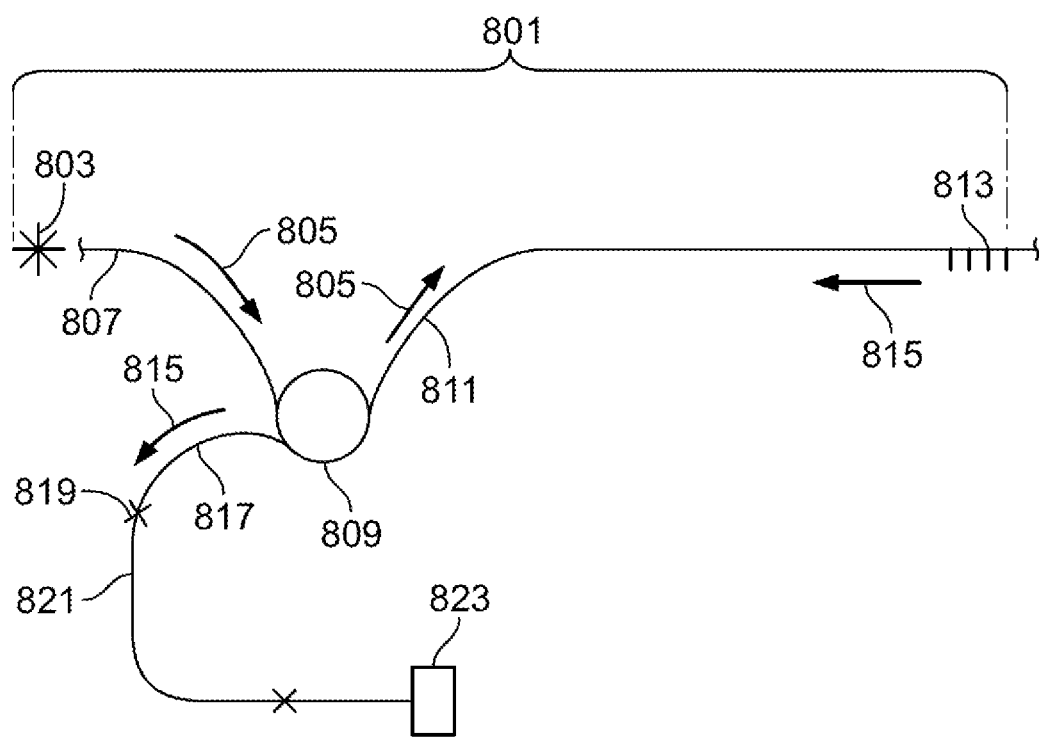
FIG. 11 is a diagram of a twist measurement system that measures changes in the polarization state of light reflected from a birefringent fiber grating written into low birefringence optical fiber.

FIG. 11 shows a variation of a system 801 that may be used to measure twist or twist angle or roll at a position along a fiber. A light source 803 that may be spectrally broad and depolarized is used to generate a light beam 805 that is coupled into the fiber end 807 and directed toward a three port circulator 809. The light beam 805 is redirected by the circulator 809 to the optical fiber 811 and the light beam propagates to a birefringent fiber grating 813 written onto the optical fiber 811.

Figure 12A:
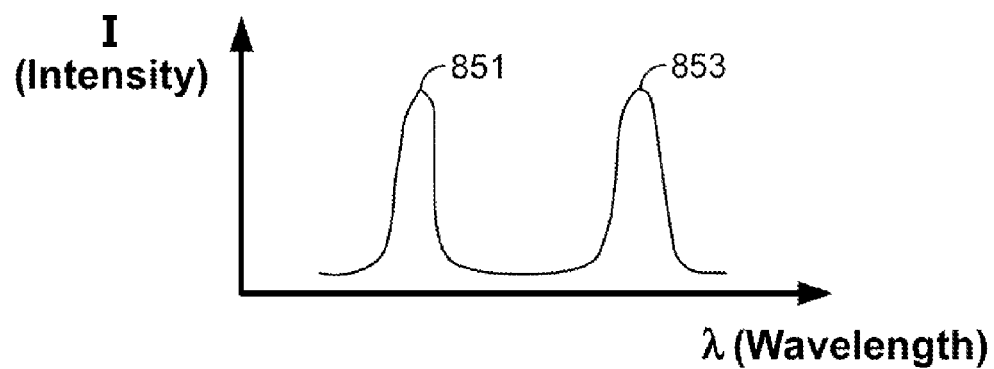
FIG. 12A is a spectral profile reflected from a birefringent fiber grating written into low birefringence optical fiber illuminated by un-polarized light
Figure 12B:
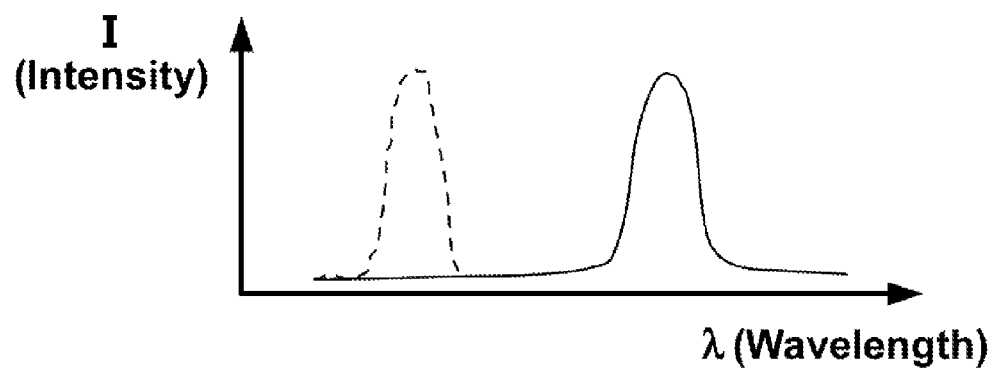
FIG. 12B is a spectral profile reflected from a birefringent fiber grating written into low birefringence optical fiber with a polarizer aligned to the polarization of one spectral peak.
Figure 12C:
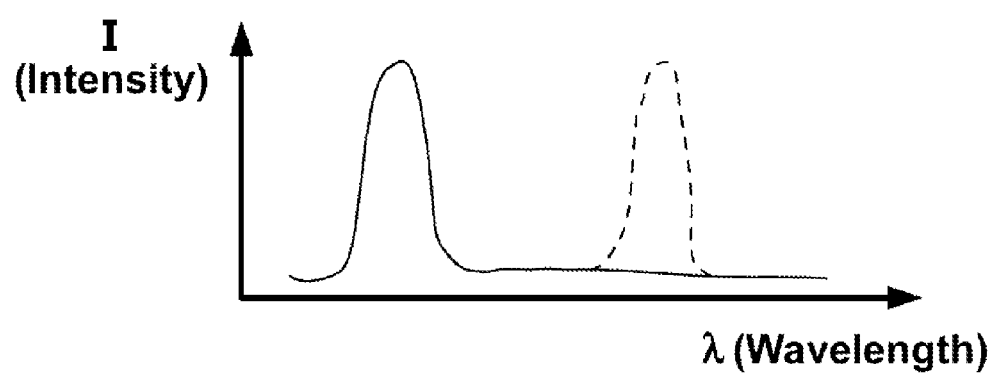
FIG. 12C is a spectral profile reflected from a birefringent fiber grating written into low birefringence optical fiber illuminated with a polarizer aligned to the second spectral peak that may be nearly orthogonal to that of FIG. 12B.

The birefringent fiber grating 813 may be made by using short femto-second light pulses that induce birefringence locally through the interaction of the light pulses with the optical fiber 811. This technique has been pioneered by the Communication Research Center in Canada. The birefringence of the optical fiber 811 causes a spectral splitting of the fiber grating 813 so that the fiber grating's reflection spectra results in two distinct spectral peaks 851 and 853 illustrated by FIG. 12a. The peaks 851 and 853 appear to have approximately equal intensity amplitude when illuminated by a depolarized light source. However the spectral peaks 851 and 853 are polarization dependent. That is, by placing a polarizer in front of the reflected spectral peaks 851 and 853 and rotating the polarizer, the spectral peak 851 can be nearly extinguished as shown in FIG. 12b. The spectral peak 853 can be nearly extinguished by rotating the polarizer to a position that is nearly orthogonal to the position where the peak 851 is extinguished as shown in FIG. 12c.

As shown in FIG. 11, the reflected light beam 815 from the birefringent fiber grating 813 is directed back to the circulator 809 and directed via the fiber segment 817 to the end 819 of the polarizer 821, which may be a fiber polarizer. The light beam 815 is then directed into the spectrometer 823 or other spectral read out system or detector that is used to measure the wavelength and amplitude of the light beam 815. When the birefringent fiber grating 813 is twisted relative to the position of the end 819 of the fiber polarizer 821, the relative amplitudes of the peaks 851 and 853 change and their ratio can be used to measure twist.

In certain variations, a two by two coupler may replace the circulator 809 and serve a similar function. Ordinary conventional single mode optical fiber with characteristics similar to Corning SMF-28 used for standard telecommunication applications may be used for all fiber in the system. The fiber used for the fiber polarizer used in the polarizer position associated with polarizer 821 may differ however. The position of the splice 819 of the polarizer end to the fiber 817 may be fixed to a table top and the birefringent fiber grating may be rotated through an angle of approximately 180 degrees. The resolution of the system may be about 2 degrees over this span. Induced birefringence due to bending or twisting of the fiber leads which may induce larger errors could be reduced by using very low birefringence optical fiber that could be fabricated using spun fiber techniques offered commercially, e.g., by Fibercore or optical fiber made by vapor axial deposition techniques offered commercially, e.g., by Sumitomo.

Optionally, for any of the systems described above and herein, the optical fibers may be bonded together as described above according to the systems of FIGS. 1-2, or a single optical fiber or large core optical fiber may be utilized or one or more optical fibers or large core optical fibers may be utilized, which are bonded or not bonded.

In certain embodiments, a fiber grating may be written into at least one of the optical fibers in such a way that the writing process results in birefringence of the fiber grating. This may be performed according to methods described in the literature and known by persons of skill in the art.

In any of the variations described herein, it is contemplated that one or more fibers may be utilized and variety of fiber types may be utilized, e.g., optical fibers, or any fibers known in the art that can support fiber gratings. In any of the variations described herein the positioning, orientation, deflection, displacement, bend, strain, yaw, pitch, roll, twist and/or temperature of the fibers may be measured.

Utilization of Fibers and Systems in Various Medical Devices and Other Systems:

Advantageously, each of the variations of shape sensing or measuring systems including fibers, e.g., optical fibers, described herein may be utilized with and to detect the movement, positioning, orientation, shape, and/or to navigate manual or robotic catheter systems, devices, or instruments, or other robotic or manual systems, instruments or devices, such as those described below. The variations of shape sensing or measuring systems may be utilized to control the positioning or navigation of various instruments, systems, and devices in a patient's body. The instruments, systems or devices may include but are not limited to, e.g., various interventional medical instruments, such as jointed positioning instruments, catheters and endoscopic devices, which may be suitable for use with Bragg and other fiber optic grating guidance systems. The various systems may also control the operation of other functions of the devices, such as imaging devices, ablation devices, cutting tools, or other end effectors. The various systems, devices or instruments may be controlled using a closed-loop servo control in which an instrument is moved in response to a command, and then the determined position may be utilized to further adjust the position. Optionally, an open loop control may be used in which an instrument is moved in response to a user command, the determined position is then displayed to the user, and the user can then input another command based on the displayed position.

The various shape sensing or measuring systems described herein may be utilized in robotic systems, robotic catheters, and/or various medical robotics for location feedback, position feedback, force feedback, and/or shape sensing or measuring.

Examples of manual and robotic catheter systems and their components and functions have been previously described in the following U.S. patent applications, which are incorporated herein by reference in their entirety for all purposes: U.S. patent application Ser. No. 10/923,660, filed Aug. 20, 2004; Ser. No. 10/949,032, filed Sep. 24, 2005; Ser. No. 11/073,363, filed Mar. 4, 2005; Ser. No. 11/173,812, filed Jul. 1, 2005; Ser. No. 11/176,954, filed Jul. 6, 2005; Ser. No. 11/179,007, filed Jul. 6, 2005; Ser. No. 11/202,925, filed Aug. 12, 2005; Ser. No. 11/331,576, filed Jan. 13, 2006; 60/785,001, filed Mar. 22, 2006; 60/788,176, filed Mar. 31, 2006; Ser. No. 11/418,398, filed May 3, 2006; Ser. No. 11/481,433, filed Jul. 3, 2006; Ser. No. 11/637,951, filed Dec. 11, 2006; Ser. No. 11/640,099, filed Dec. 14, 2006; 60/833,624, filed Jul. 26, 2006 and 60/835,592, filed Aug. 3, 2006; Ser. No. 12/012,795, filed Feb. 1, 2008; Ser. No. 12/106,254, filed Apr. 18, 2008; Ser. No. 11/690,116, filed Mar. 22, 2007; Ser. No. 12/822,876 filed Jun. 24, 2010; Ser. No. 12/823,012 filed Jun. 24, 2010; Ser. No. 12/823,032 filed Jun. 24, 2010.

Certain of the variations described herein may be utilized with manually or robotically steerable instruments, such as those described in the aforementioned patent application, U.S. Ser. No. 11/481,433. In addition, all of the variations may be utilized with the manual or robotic catheter systems and methods described in the U.S. patent applications listed above, and incorporated by reference herein in their entirety for all purposes and/or the manual or robotic catheter systems described below.

Figure 13:
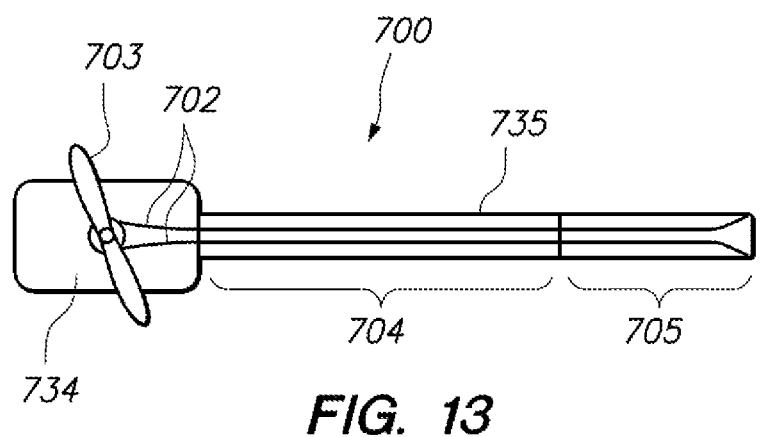
FIG. 13 illustrates a conventional manually-steerable catheter.

For example, referring to FIG. 13, the shape sensing or measuring systems described herein may be utilized with a conventional manually-steerable catheter 700. In operating 700, pullwires 702 may be selectively tensioned through manipulation of a handle 703 on the proximal portion of the catheter structure 700 to make a more flexible distal portion 705 of the catheter bend or steer controllably. The handle (703) may be coupled, rotatably or slidably, for example, to a proximal catheter structure (734) which may be configured to be held in the hand, and may be coupled to the elongate portion (735) of the catheter (700). A more proximal and conventionally less steerable portion 704 of the catheter may be configured to be compliant to loads from surrounding tissues (for example, to facilitate passing the catheter, including portions of the proximal portion, through tortuous pathways such as those formed by the blood vessels), yet less steerable as compared with the distal portion 705.

Figure 14:
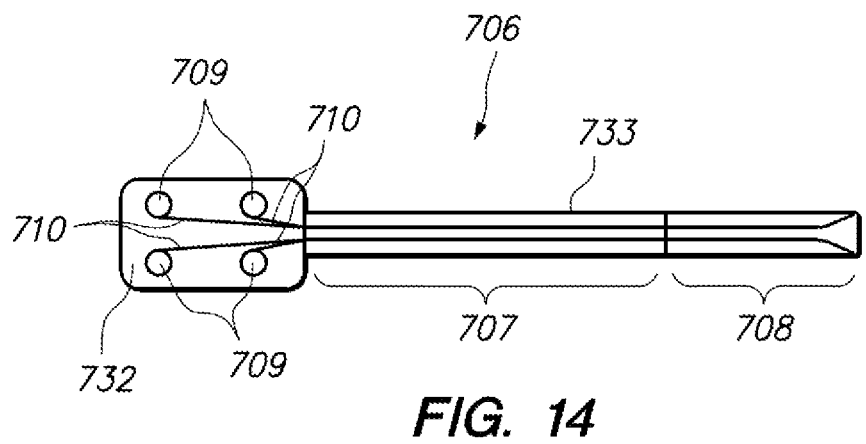
FIG. 14 illustrates a variation of a robotically-driven steerable catheter.

Referring to FIG. 14, the shape sensing or measuring systems described herein may be utilized with a robotically-driven steerable catheter 706, e.g., similar to those described in detail in U.S. patent application Ser. No. 11/176,598, incorporated by reference herein in its entirety for all purposes. This catheter 706 has some similarities with the manually-steerable catheter 700 of FIG. 13 in that it has pullwires or similar control elements 710 associated distally with a more flexible section 708 configured to steer or bend when the pullwires or control elements 710 are tensioned in various configurations, as compared with a less steerable proximal portion 707 configured to be stiffer and more resistant to bending or steering. The control elements can be flexible tendons or pullwires, or other mechanical structures that allow for steering or deflection of the catheter (706). The depicted variation of the robotically-driven steerable catheter 706 comprises proximal axles or spindles 709 configured to primarily interface not with fingers or the hand, but with an electromechanical instrument driver configured to coordinate and drive, with the help of a computer, each of the spindles 709 to produce precise steering or bending movement of the catheter 706. The spindles (709) may be rotatably coupled, e.g., via pullwires, to a proximal catheter structure (732) which may be configured to mount to an electromechanical instrument driver apparatus, such as that described in the aforementioned U.S. patent application Ser. No. 11/176,598, and may be coupled to the elongate portion (733) of the catheter (706). The spindles 709 may be the same or similar to the control element interface assemblies which can be controlled by an instrument drive assembly as shown and described in U.S. patent application Ser. No. 11/637,951.

Each of the variations depicted in FIGS. 13 and 14 may have a working lumen (not shown) located, for example, down the central axis of the catheter body, or may be without such a working lumen. If a working lumen is formed by the catheter structure, it may extend directly out the distal end of the catheter, or may be capped or blocked by the distal tip of the catheter. It is highly useful in many procedures to have precise information regarding the spatial position or shape of the distal portion or tip or body of catheters or other elongate instruments, such as those available from suppliers such as the Ethicon Endosurgery division of Johnson & Johnson, or Intuitive Surgical Corporation, during diagnostic or interventional procedures. The shape sensing or measuring systems described herein may be incorporated or integrated in such catheter, sheaths or instruments to provide information regarding spatial position, shape, twist, roll, orientation, etc., of the catheters, sheaths or instruments. The examples and illustrations that follow are made in reference to a robotically-steerable catheter such as that depicted in FIG. 14, but as would be apparent to one skilled in the art, the same principles may be applied to other elongate instruments, such as the manually-steerable catheter depicted in FIG. 13, or other elongate instruments, highly flexible or not, from suppliers such as the Ethicon Endosurgery division of Johnson & Johnson, Inc., or Intuitive Surgical, Inc.

Figure 15A:
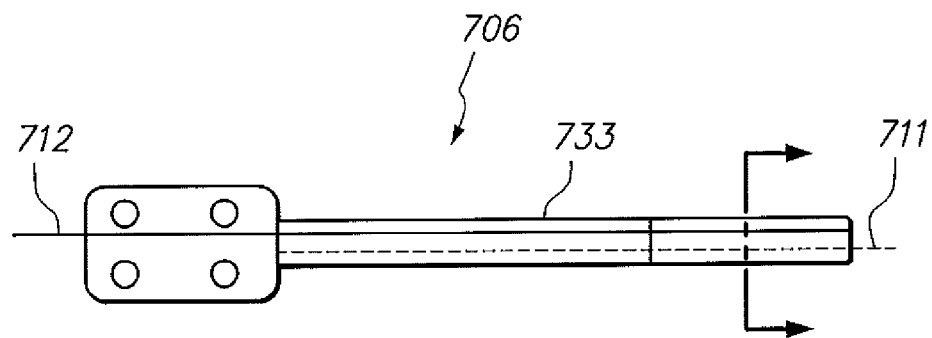
FIGS. 15A-15C illustrate a variation of a robotically-steerable catheter having an optical fiber positioned along the wall of the catheter.
Figure 15B:
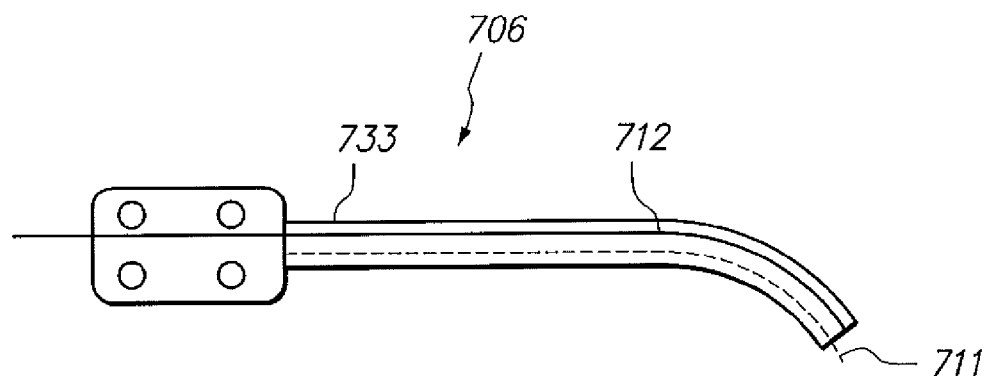
Figure 15C:
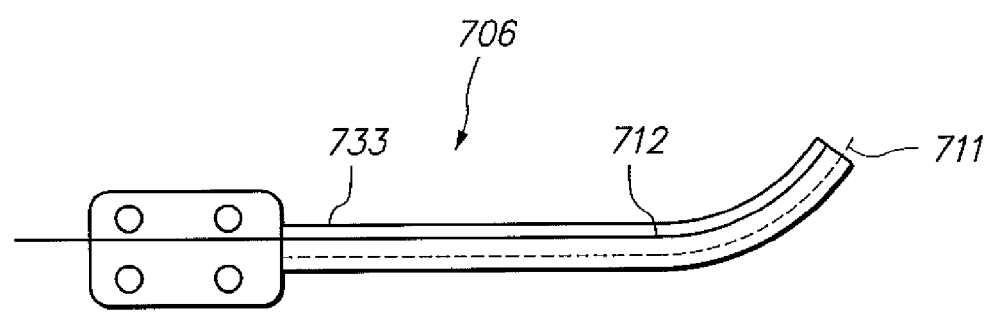

Referring to FIGS. 15A-15C, a variation of a robotically-steerable catheter 706 is depicted having an optical fiber 712. The fiber may be a fiber shape sensing or measuring system according to any of the embodiments described herein. The fiber 712 may be positioned along one aspect of the wall of the catheter 706. The fiber is not positioned coaxially with the neutral axis of bending 711 in the bending scenarios depicted in FIGS. 15B and 15C. Indeed, with the fiber 712 attached to, or longitudinally constrained by, at least two different points along the length of the catheter 706 body and unloaded from a tensile perspective relative to the catheter body 733 in a neutral position of the catheter body 733 such as that depicted in FIG. 15A, the longitudinally constrained portion of the fiber 712 would be placed in tension when the catheter 706 is deflected as depicted in FIG. 15B, while the longitudinally constrained portion of the fiber 712 would be placed in compression when the catheter 106 is deflected as depicted in FIG. 15C. Such relationships are elementary to solid mechanics, but may be applied as described herein with the use of an optical fiber grating to assist in the determination of e.g., temperature, displacement, shape, and/or deflection of an elongate instrument. The optical fiber grating can comprise a Bragg or other grating. Examples of fiber optic Bragg fiber sensing technology may be available from Luna Innovations, Inc. of Roanoke, Va., Micron Optics, Inc., of Atlanta, Ga., LxSix Photonics, Inc., of Quebec, Canada, and Ibsen Photonics A/S, of Denmark.

Referring to FIGS. 16A-17D, several different embodiments which can incorporate the shape sensing or measuring systems described herein are depicted. Referring to FIG. 16A, a robotic catheter (706) is depicted having a shape sensing or measuring fiber (712) deployed through a lumen (731) which extends from the distal tip of the distal portion (708) of the catheter body (733) to the proximal end of the proximal catheter structure (732). In one embodiment a broadband reference reflector may be positioned near the proximal end of the fiber in an operable relationship with the optical grating wherein an optical path length is established for each reflector/grating relationship comprising the subject fiber grating sensor configuration; additionally, such configuration may also comprise a reflectometer, such as a frequency domain reflectometer, to conduct spectral analysis of detected reflected portions of light waves.

Constraints (730) may be provided to prohibit axial or longitudinal motion of the fiber (712) at the location of each constraint (730). Alternatively, the constraints (730) may only constrain the position of the fiber (712) relative to the lumen (731) in the location of the constraints (730). For example, in one variation of the embodiment depicted in FIG. 16A, the most distal constraint (730) may be configured to disallow longitudinal or axial movement of the fiber (712) relative to the catheter body (733) at the location of such constraint (730), while the more proximal constraint (730) may merely act as a guide to lift the fiber (712) away from the walls of the lumen (731) at the location of such proximal constraint (730). In another variation of the embodiment depicted in FIG. 16A, both the more proximal and more distal constraints (730) may be configured to disallow longitudinal or axial movement of the fiber (712) at the locations of such constraints, and so on. As shown in the embodiment depicted in FIG. 16A, the lumen (731) in the region of the proximal catheter structure (732) is without constraints to allow for free longitudinal or axial motion of the fiber relative to the proximal catheter structure (732). Constraints configured to prohibit relative motion between the constraint and fiber at a given location may comprise small adhesive or polymeric welds, interference fits formed with small geometric members comprising materials such as polymers or metals, locations wherein braiding structures are configured with extra tightness to prohibit motion of the fiber, or the like. Constraints configured to guide the fiber (712) but to also allow relative longitudinal or axial motion of the fiber (712) relative to such constraint may comprise small blocks, spheres, hemispheres, etc defining small holes, generally through the geometric middle of such structures, for passage of the subject fiber (712).

The embodiment of FIG. 16B is similar to that of FIG. 16A, with the exception that there are two additional constraints (730) provided to guide and/or prohibit longitudinal or axial movement of the fiber (712) relative to such constraints at these locations. In one variation, each of the constraints is a total relative motion constraint, to isolate the longitudinal strain within each of three "cells" provided by isolating the length of the fiber (712) along the catheter body (733) into three segments utilizing the constraints (730). In another variation of the embodiment depicted in FIG. 16B, the proximal and distal constraints (730) may be total relative motion constraints, while the two intermediary constraints (730) may be guide constraints configured to allow longitudinal or axial relative motion between the fiber (712) and such constraints at these intermediary locations, but to keep the fiber aligned near the center of the lumen (731) at these locations.

Referring to FIG. 16C, an embodiment similar to those of FIGS. 16A and 16B is depicted, with the exception that entire length of the fiber that runs through the catheter body (733) is constrained by virtue of being substantially encapsulated by the materials which comprise the catheter body (733). In other words, while the embodiment of FIG. 16C does have a lumen (731) to allow free motion of the fiber (712) longitudinally or axially relative to the proximal catheter structure (732), there is no such lumen defined to allow such motion along the catheter body (733), with the exception of the space naturally occupied by the fiber as it extends longitudinally through the catheter body (733) materials which encapsulate it.

FIG. 16D depicts a configuration similar to that of FIG. 16C with the exception that the lumen (731) extends not only through the proximal catheter structure (732), but also through the proximal portion (707) of the catheter body (733); the distal portion of the fiber (712) which runs through the distal portion of the catheter body (733) is substantially encapsulated and constrained by the materials which comprise the catheter body (733).

Figure 17A:
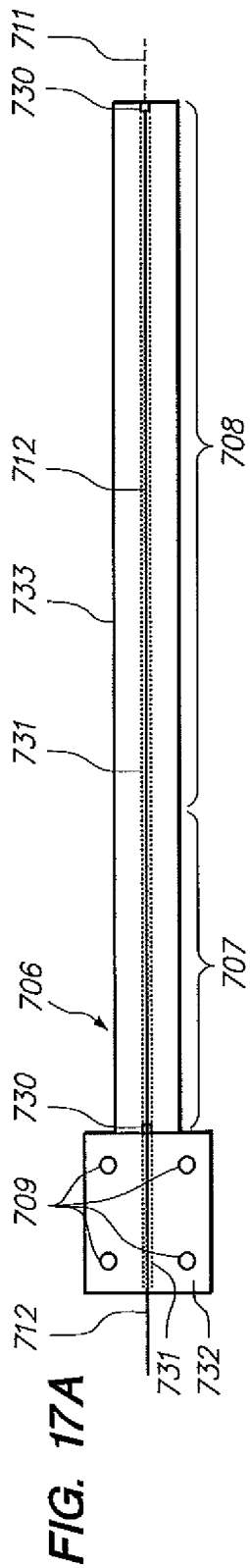
FIGS. 17A-17D illustrate implementation of an optical fiber with a grating to an elongate instrument such as a robotically-steerable catheter.
Figure 17B:
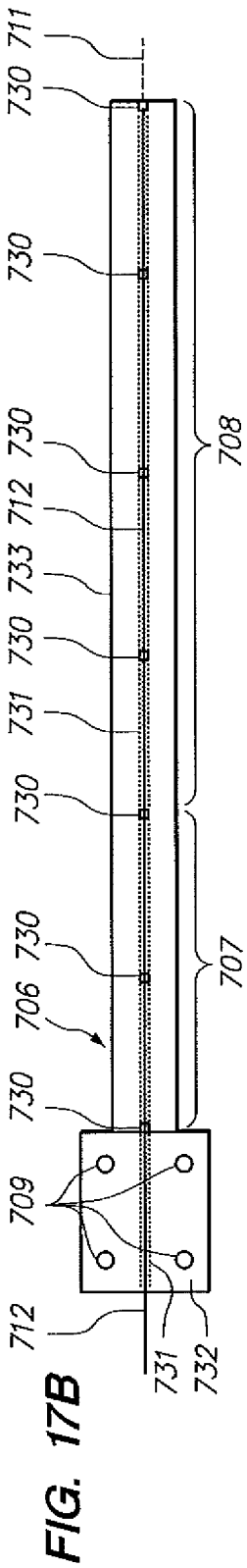
Figure 17C:
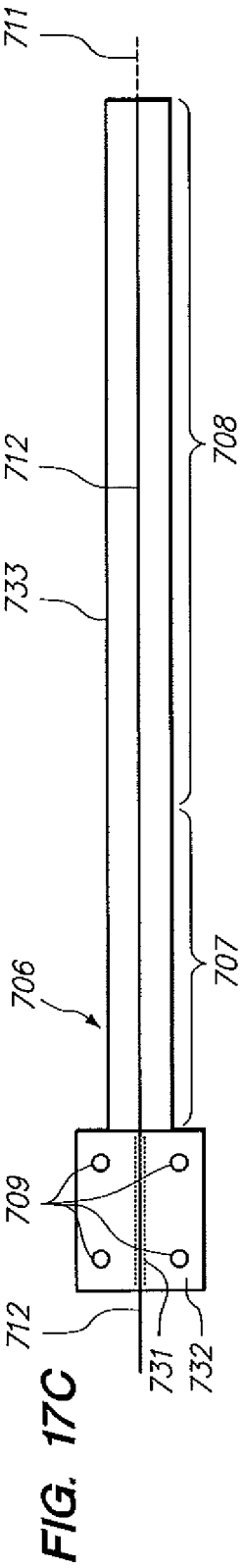
Figure 17D:
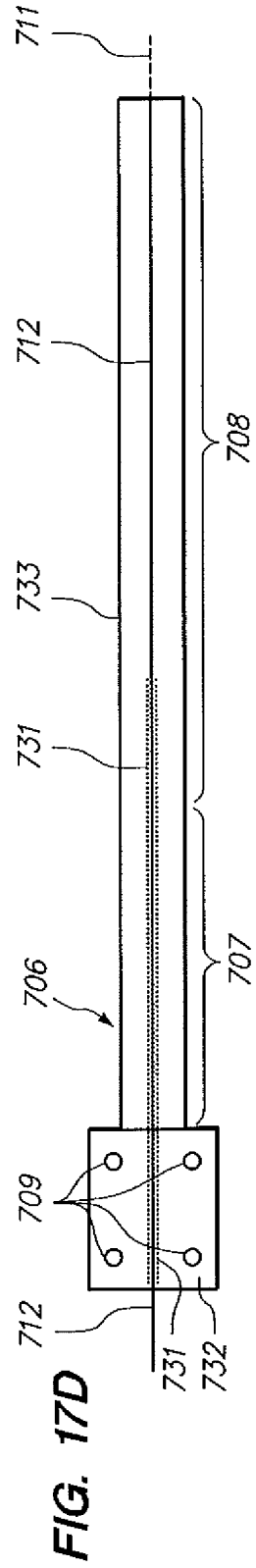

FIGS. 17A-17D depict embodiments analogous to those depicted in FIGS. 16A-D, with the exception that the fiber (12) is positioned substantially along the neutral axis of bending (711) of the catheter body (733), and in the embodiment of FIG. 17B, there are seven constraints (730) as opposed to the three of the embodiment in FIG. 16B.

Figure 18:
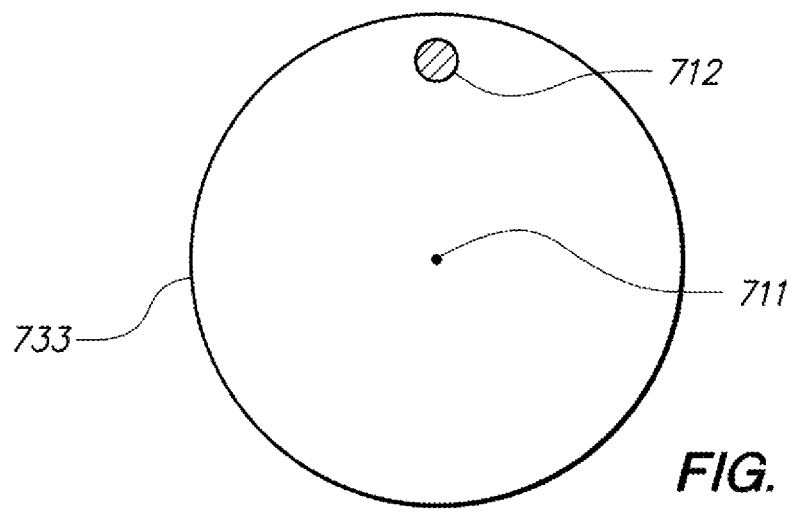
FIG. 18 illustrates a cross sectional view of an elongate instrument such as a catheter including an optical fiber with optical gratings.
Figure 19:
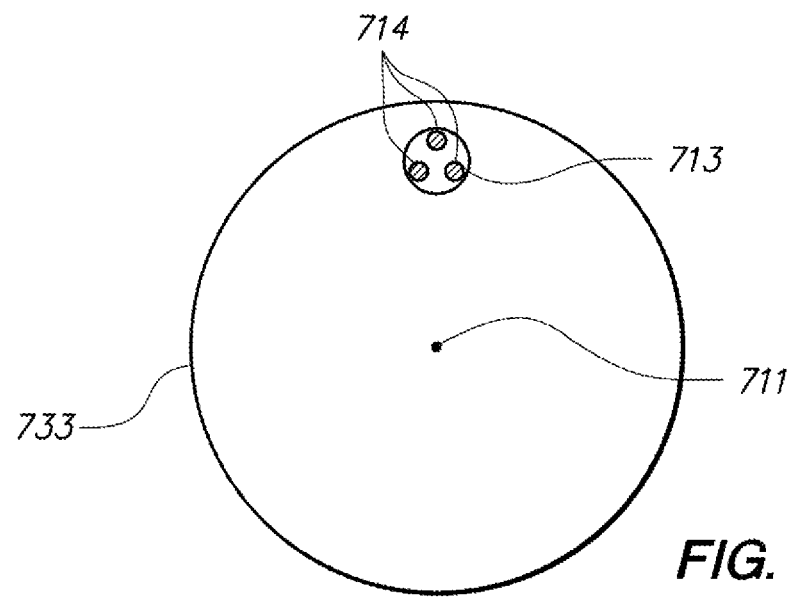
FIG. 19 illustrates a cross sectional view of an elongate instrument such as a catheter including a multi-fiber optical grating configuration.
Figure 20:
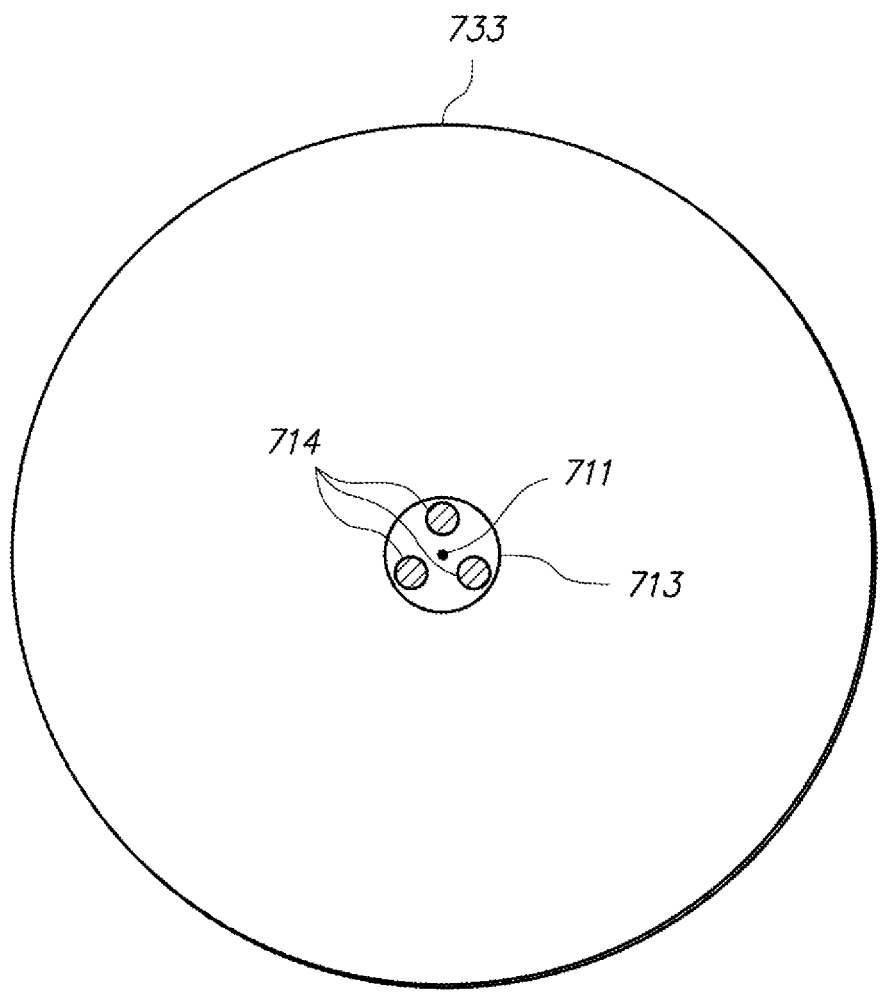
FIG. 20 illustrates a cross sectional view of an elongate instrument such as a catheter including a multi-fiber grating configuration.
Figures 21A, 21B:
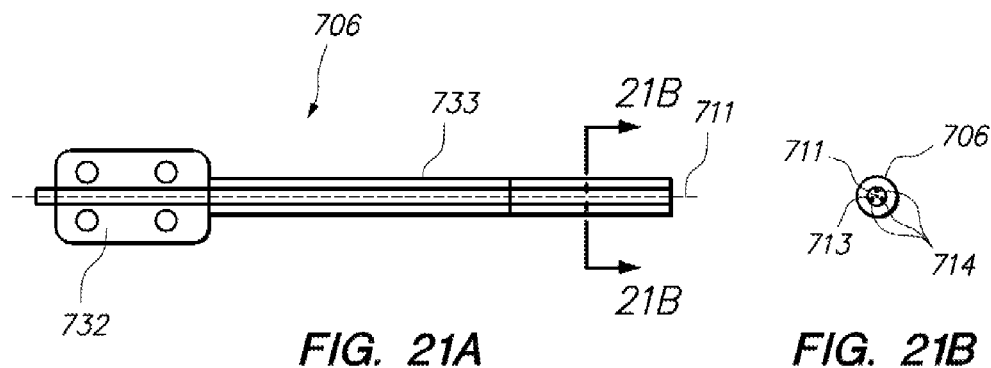
FIGS. 21A-21B illustrate top and cross sectional views of an elongate instrument such as a catheter having a multi-fiber structure with optical gratings.
Figures 22A, 22B:
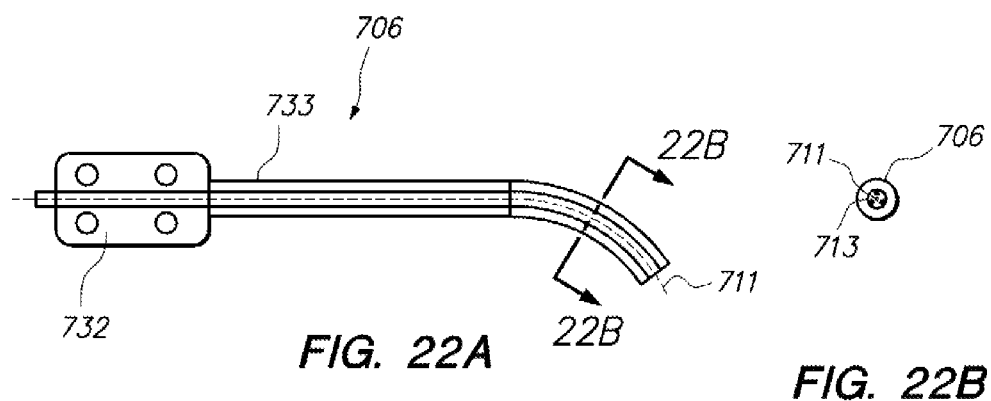
FIGS. 22A-22B illustrate top and cross sectional views of an elongate instrument such as a catheter having a multi-fiber structure with optical gratings.
Figures 23A, 23B:
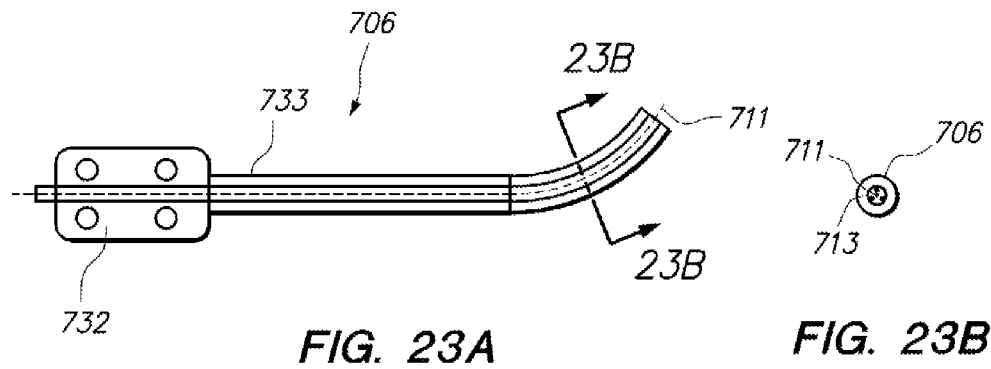
FIGS. 23A-23B illustrate top and cross sectional views of an elongate instrument such as a catheter having a multi-fiber structure with optical gratings.

Referring to FIG. 18, a cross section of a portion of the catheter body (733) of the configuration depicted in FIG. 16C is depicted, to clearly illustrate that the fiber (712) is not placed concentrically with the neutral axis (711) of bending for the sample cross section. FIG. 19 depicts a similar embodiment, wherein a multi-fiber bundle (713), such as those available from Luna Technologies, Inc., is positioned within the wall of the catheter rather than a single fiber as depicted in FIG. 18, the fiber bundle (713) comprising multiple, in this embodiment three, individual (e.g., smaller) fibers or fiber cores (714). When a structure such as that depicted in FIG. 19 is placed in bending in a configuration such as that depicted in FIG. 15B or 15C, the most radially outward (from the neutral axis of bending (711)) of the individual fibers (714) experiences more compression or tension than the more radially inward fibers. Alternatively, in an embodiment such as that depicted in FIG. 20, which shows a cross section of the catheter body (733) portion a configuration such as that depicted in FIG. 17C, a multi-fiber bundle (713) is positioned coaxially with the neutral axis of bending (711) for the catheter (706), and each of three individual fibers (714) within the bundle (713) will experience different degrees of tension and/or compression in accordance with the bending or steering configuration of the subject catheter, as would be apparent to one skilled in the art. For example, referring to FIGS. 21A and 21B (a cross section), at a neutral position, all three individual fibers (714) comprising the depicted bundle (713) may be in an unloaded configuration. With downward bending, as depicted in FIGS. 22A and 22B (a cross section), the lowermost two fibers comprising the bundle (713) may be configured to experience compression, while the uppermost fiber experiences tension. The opposite would happen with an upward bending scenario such as that depicted in FIGS. 23A and 23B (cross section).

Indeed, various configurations may be employed, depending upon the particular application, such as those depicted in FIGS. 24A-24H. For simplicity, each of the cross sectional embodiments of FIGS. 24A-24H is depicted without reference to lumens adjacent the fibers, or constraints (i.e., each of the embodiments of FIGS. 24A-24H are depicted in reference to catheter body configurations analogous to those depicted, for example, in FIGS. 16C and 17C, wherein the fibers are substantially encapsulated by the materials comprising the catheter body (733); additional variations comprising combinations and permutations of constraints and constraining structures, such as those depicted in FIGS. 4A-5D, are within the scope of this invention. FIG. 24A depicts an embodiment having one fiber (712). FIG. 24B depicts a variation having two fibers (712) in a configuration capable of detecting tensions sufficient to calculate three-dimensional spatial deflection of the catheter portion. FIG. 24C depicts a two-fiber variation with what may be considered redundancy for detecting bending about a bending axis such as that depicted in FIG. 24C. FIGS. 24D and 24E depict three-fiber configurations configured for detecting three-dimensional spatial deflection of the subject catheter portion. FIG. 24F depicts a variation having four fibers configured to accurately detect three-dimensional spatial deflection of the subject catheter portion. FIGS. 12G and 12H depict embodiments similar to 24B and 24E, respectively, with the exception that multiple bundles of fibers are integrated, as opposed to having a single fiber in each location. Each of the embodiments depicted in FIGS. 24A-24H, each of which depicts a cross section of an elongate instrument comprising at least one optical fiber, may be utilized to facilitate the determination of bending deflection, torsion, compression or tension, and/or temperature of an elongate instrument.

In essence, the 3-dimensional position, shape, twist or roll of an elongate member may be determined by determining the incremental curvature experienced along various longitudinal sections of such elongate member. In other words, if you know how much an elongate member has curved in space at several points longitudinally down the length of the elongate member, you can determine the position of the distal portion and more proximal portions in three-dimensional space by virtue of the knowing that the sections are connected, and where they are longitudinally relative to each other. Towards this end, variations of embodiments such as those depicted in FIGS. 24A-24H may be utilized to determine the position of a catheter or other elongate instrument in 3-dimensional space. To determine local curvatures at various longitudinal locations along an elongate instrument, fiber optic grating analysis may be utilized.

The various shape sensing or measuring systems and/or fibers described herein may be integrated or incorporated in various elongate members or instruments such as manual or robotic catheters or catheter guide instruments or sheath instruments to sense or measure the shape, twist, roll, position, orientation, etc. of such members and/or instruments.

Figure 25A:
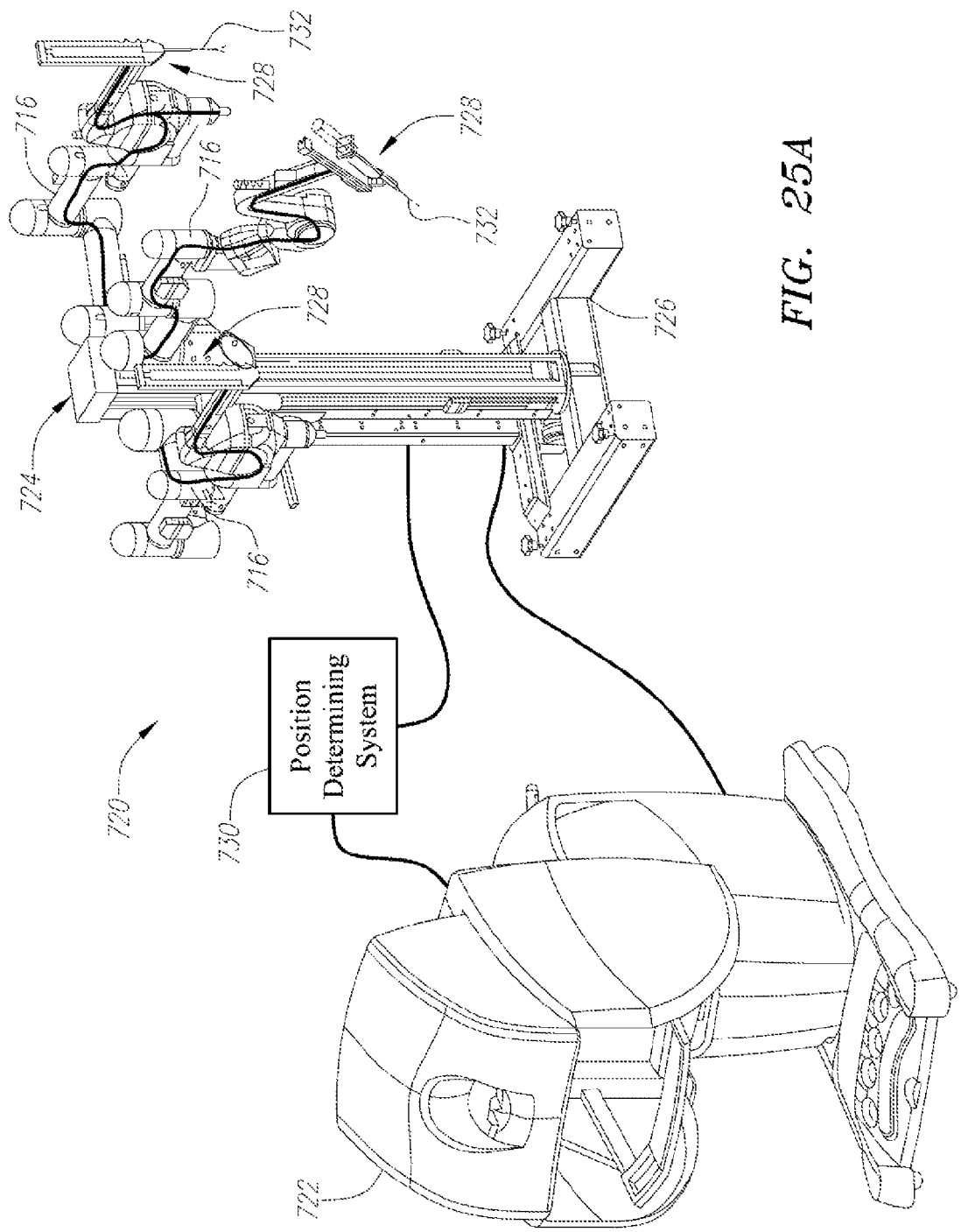
FIG. 25A-25B show a perspective view of a surgical system with a shape sensing system mounted thereon.

Referring to FIG. 25A, the shape sensing or measuring systems described herein may also be utilized with various robotic surgical instruments or systems, e.g., the "da Vinci Surgical System" available from Intuitive Surgical Inc. of Sunnyvale, Calif. FIG. 25A illustrates a perspective view of a da Vinci telesurgical system 720 including its operator control station 722 and surgical workstation 724. The surgical workstation 724 comprises a cart 726, which supports the robotic arms 728. One or more fibers 716, (e.g., a shape sensing or measuring systems including optical fibers and/or Bragg fiber sensors or gratings) according to the variations described herein may be disposed along at least a portion of the length of each arm 728. Alternatively, multiple fibers 716 may be disposed on each arm 728. For example, separate fiber 716 may be disposed on each link of the robotic arm 728. In the depicted variations, fiber 716 may be operably coupled to interventional and/or diagnostic instruments, such as the depicted robotic arm 728, utilizing bands, clips, fasteners, a layer of at least partially encapsulating material, or the like, distributed along the length of the robotic arm or other structure to maintain the position of the fiber 716 relative to the position of the pertinent portions of such structure.

Referring again to FIG. 25A, a position determining system 730 is depicted operatively coupled to each of the fibers 716. The position determining system 730, generally comprising an optical radiation emitter and detector, and a computing system to analyze detected optical radiation, may be operatively coupled to each of the fibers 716 via the cart 726. The position determining system 730 is configured to analyze data from the fibers 716 as the arms 728 are maneuvered and determine changes in elongation of the fibers 716. Some systems, such as those available from Luna Innovations, Inc., may be configured to utilize sensed deflection data to determine the spatial positioning or shape of a particular fiber or bundle of fibers. Although it is referred to herein as a "position determining system," such system may also analyze, calculate and/or determine other information using the data from the fibers, including without limitation, stress, strain or elongation, forces, and/or temperature. The positioning determining system 730 is also operatively coupled to the operator control station 722 or control system of the instrument system, such that position information as determined by the position determining system 730 may be relayed to the operator control system 722 to assist in navigation and control of the instrument system. In this illustration, the surgical workstation 724 carries three robotically controlled arms 728, and the movement of the arms 728 is remotely controllable from the control station 722. In other variations, the cart 726 may carry a varying number of arms 728 (i.e., one or more arms; or two or four arms) depending on the particular configuration.

Figure 25B:
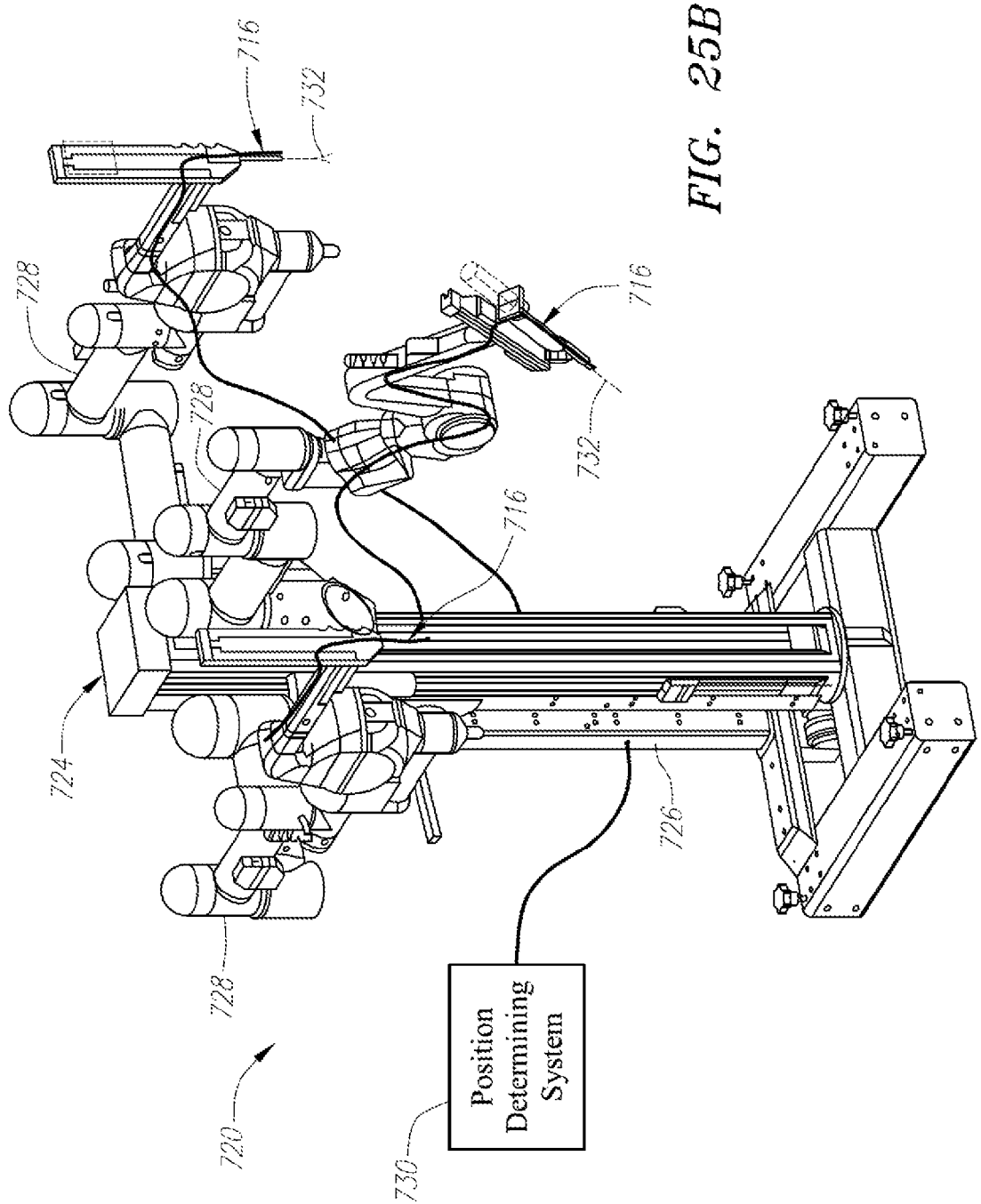

Referring to FIG. 25B, telesurgical system 720 includes a cart 726 carrying three robotically controlled manipulator arms 728, each having a fiber 716 disposed thereon, and extending along the catheters 732 operatively coupled to the arms 728. In one variation, the fibers 716 may be routed through the support structure of the arms 728 to the catheters 732. In another variation, the fibers 716 may be freely connected from a position determining system 730 directly to each of the catheter assemblies 732.

The fibers or shape sensing or measuring systems have been described as being disposed on, coupled to or located on a robotic arm, instrument, catheter, and/or tool. In addition, it is contemplated that in some variations, the fibers or fiber bundles may be mounted to or installed on the exterior surface or housing of the robotic instrument. For example, one or more fibers may be routed on the external housing of a robotic arm of the Intuitive Surgical da Vinci system, a Mako system, or a Accuray system. Similarly, one or more fibers may be fastened on the outer surface of the instrument of a Intuitive Surgical, Stereotaxis, or NeoGuide system or apparatus. Furthermore, a fiber may be attached to a tool instrument or end-effector which may be operably coupled with the distal end of an instrument.

It is further contemplated that in alternative variations, the fibers may be installed within or integrated into the robotic instrument itself. For example, one or more fiber sensors may be routed internally to the robotic arm of a Intuitive Surgical da Vinci system, a Mako system, or a Accuray system. Similarly, one or more fibers may be located within the catheter instrument of a Intuitive Surgical catheter, Stereotaxis catheter, or NeoGuide catheter. Furthermore, a fiber may be built into a tool instrument or end-effector at the distal end of a catheter instrument. Accordingly, as used herein, the term "disposed on" shall include without limitation all of these described methods of providing the described structure with a fiber or shape sensing or measuring system, and shall not be limited to any particular mounting method or location relative to the structure.

Figure 26A:
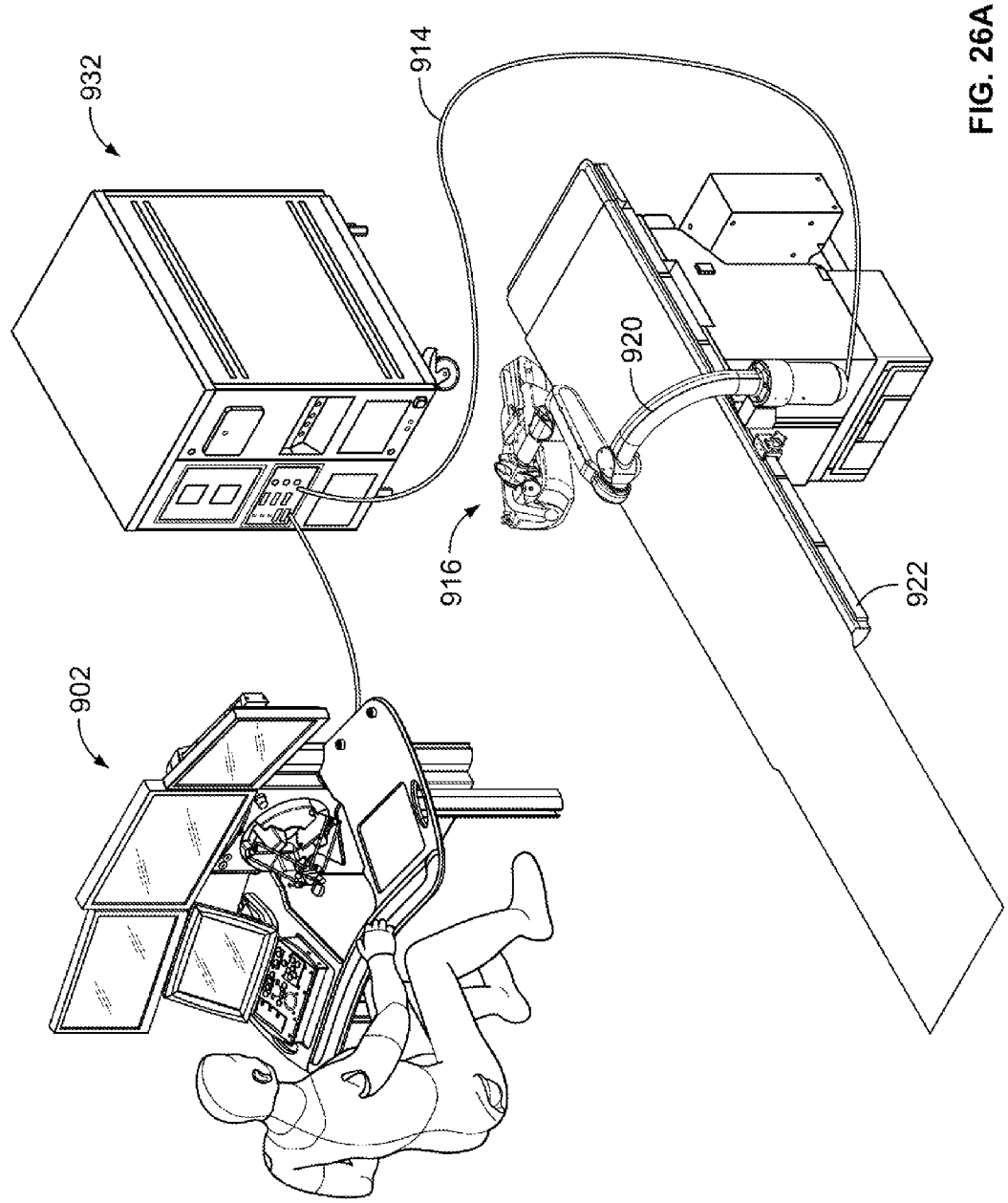
FIG. 26A-26C show a variation of a robotic surgical system.
Figure 26B:
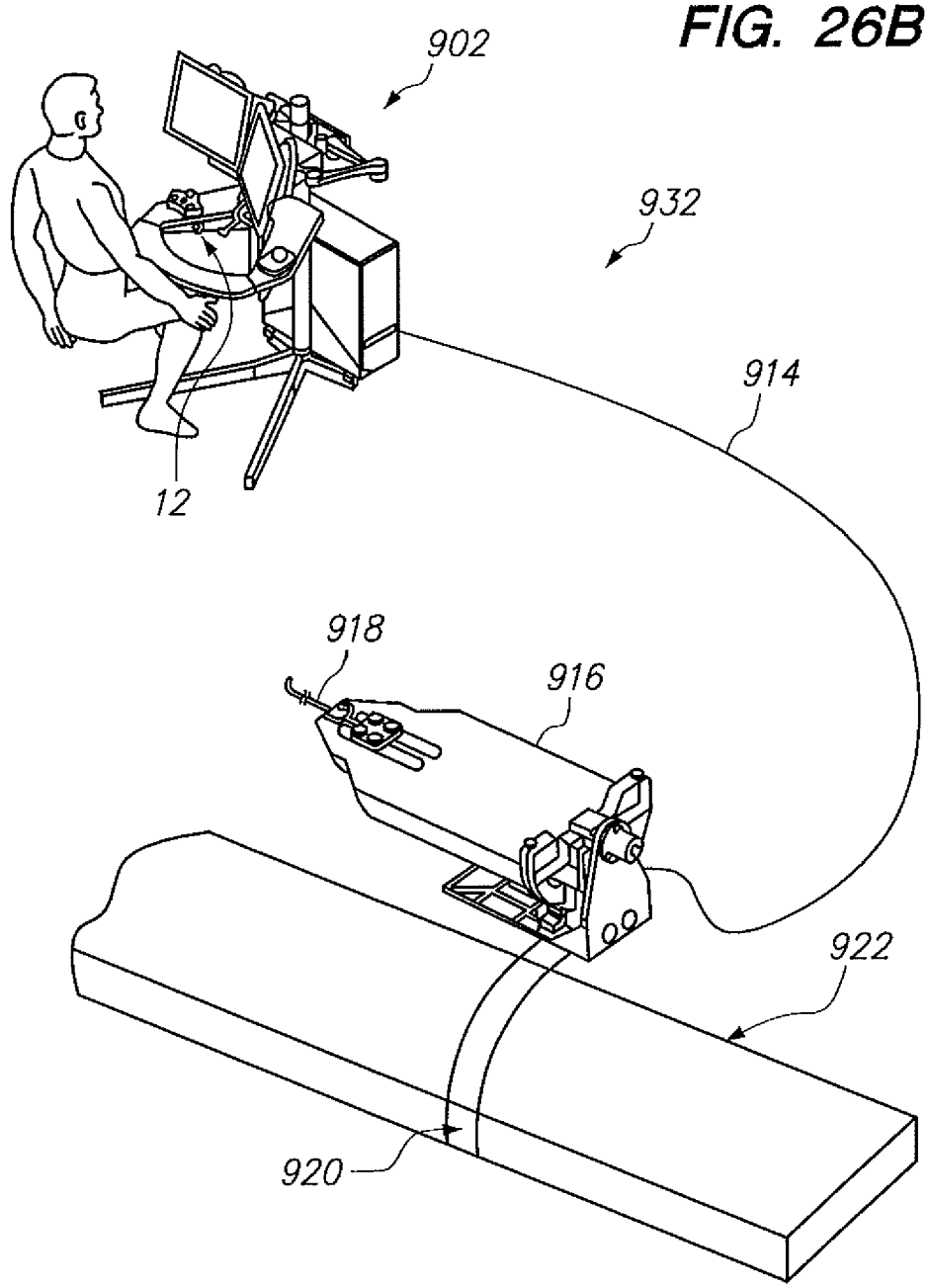
Figure 26C:
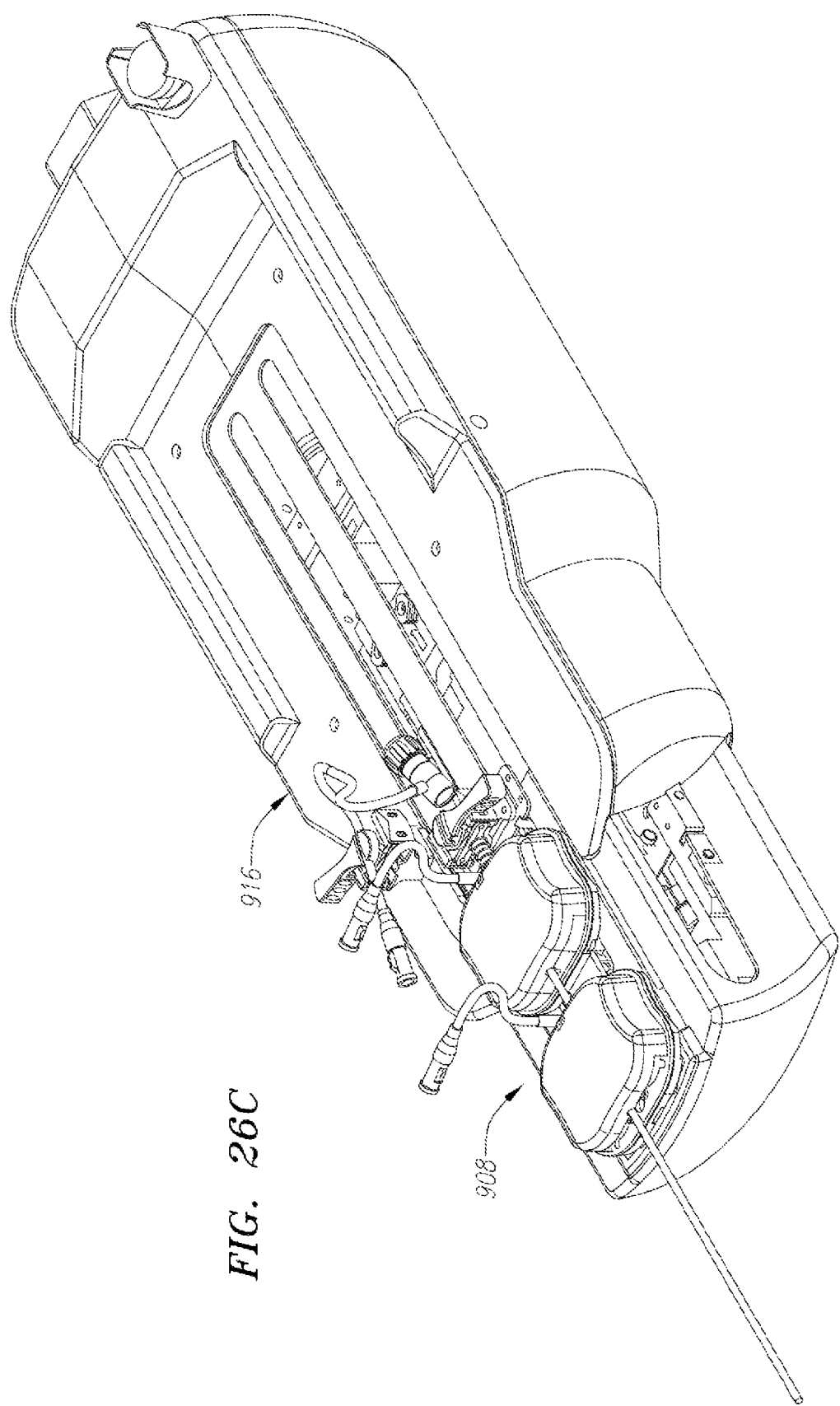

Referring to FIGS. 26A-26B, the shape sensing or measuring systems described herein may also be utilized or incorporated with various robotic catheter surgical instruments or systems to detect or sense the shape, bend or twist of the elongate instruments, members or catheters of the systems shown in FIGS. 26A-26B. For example, variations of a robotic catheter system 932, may include an operator control station 902 located remotely from an operating table 922, to which a instrument driver 916 and instrument 918 are coupled by a instrument driver mounting brace 920. A communication link 914 transfers signals between the operator control station 902 and instrument driver 916 via an electronics rack housing PCBs or other electronic equipment. The instrument driver mounting brace 920 of the depicted embodiment is a relatively simple, arcuate-shaped structural member configured to position the instrument driver 916 above a patient (not shown) lying on the table 922. Examples of systems in which the shape sensing or measuring systems described herein may be incorporated to measure and sense shape, position, etc. of such systems include, the Sensei™ Robotic Catheter System from Hansen Medical, Inc. in Mountain View, Calif., U.S.A. and the Artisan™ Control Catheter also from Hansen Medical, Inc. in Mountain View, Calif., U.S.A. The shape sensing or measuring systems described herein may be utilized or incorporated into a robotic medical system for controlling a shapeable instrument or elongate member within an anatomical region. The shapeable instrument or elongate member may include at least a working section and one or more positioning elements that move the shapeable instrument. The medical system may include a controller including a master input device, where the controller generates a position control signal in response to the master input device to position the working section at a desired position. The system may include one or more actuators operatively coupleable to the one or more positioning elements, where the actuators manipulate the positioning elements based on the position control signal to drive at least a first portion of the shapeable instrument to position the working section toward the desired position. The actuators may be driven by an instrument driver. The system may include a localization system (which may include optical fibers as described herein) which is configured to obtain a plurality of localized shape data from the first portion of the shapeable instrument and the controller may generate a signal based upon a differential between the localized shape data and a desired configuration of the first portion of the shapeable instrument.

The systems, devices, and methods described herein may be utilized to control various shapeable medical instruments. Shapeable medical instruments, in most variations described herein, include any steerable devices, flexible catheters or more rigid arms or shafts whether such devices are used to access a region for advancement of a treatment device, or any actual shapeable treatment device. A shapeable device as used herein includes flexible, steerable, or otherwise positionable devices that are advanced to various tissue structures within the body. Such devices can assume a shaped configuration via manipulation or steering. Moreover, shapeable devices include those flexible devices that conform to anatomic or other obstructions. In many variations, shapeable instruments include a working end and one or more positioning elements that move the shapeable instrument. In one example, the positioning elements comprise control elements such as tendons wires, or other mechanical structures that are moved by one or more actuators to affect a shape or reposition the shapeable instrument. Unless specifically used to indicate a particular device, the term catheter is one example of a shapeable instrument.

In one variation, the robotic medical system comprises a medical system for controlling a shapeable instrument within an anatomical region, where the shapeable instrument includes at least a working section and one or more positioning elements that move the shapeable instrument.

One variation of the system includes a controller including a master input device, where the controller generates a position control signal in response to the master input device to position the working section at a desired position; one or more actuators operatively coupleable to the one or more positioning elements, where the actuators manipulate the positioning elements based on the position control signal to drive at least a first portion of the shapeable instrument to position the working section toward the desired position; a localization system configured to obtain a plurality of localized shape data from the first portion of the shapeable instrument; and where the controller generates a signal based upon a differential between the localized shape data and a desired configuration of the first portion of the shapeable instrument. The desired configuration of the first portion can include a desired position of the first portion or the desired position of the working section. Alternatively, or in combination, the desired configuration of the first portion comprises a desired shape of the first portion.

The localization system can determine a position of the working section from the plurality of localized shape data. In another variation, the desired configuration of the first portion comprises a desired position of the first portion and where controller generates the signal based upon the differential between the position of the working section and the desired position of the working section. The controller of the robotic medical system can be configured to derive a position of the working section from a kinematic model of the shapeable instrument.

A variation of the robotic medical system includes a localization system that determines a shape of the first portion of the shapeable instrument from the plurality of localized shape data. The desired configuration of the first portion can comprises a desired shape of the first portion and where controller generates the signal based upon the differential between the shape of the first portion and the desired shape of the first portion. In another variation, the localization system also determines a position of the working section from the plurality of localized shape data, and where the desired configuration of the first portion also includes a desired position of the first portion.

In another variation, the controller generates the signal also based upon the differential between a desired position of the first portion and the position of the first portion.

The robotic medical system can also include a controller that is configured to feed the signal to the actuators such that the actuators manipulate one or more of the positioning elements using the signal to position the working section or the first portion of the shapeable instrument.

In one variation, the localization system comprises a fiber optic localization system configured to supply the plurality of localization data. Furthermore, the shapeable instrument can include at least one optic fiber and where the localization system is configured to measure a plurality of data of Rayleigh scatter of the optic fiber. The Rayleigh scatter data can be used to supplement or supply the localization data.

In one example, a shapeable instrument comprises an elongate instrument body; an optical fiber coupled in a constrained manner to the elongate instrument body, the optical fiber is in communication with one or more optical gratings; and a detector operably coupled to a proximal end of the optical fiber and configured to detect respective light signals reflected by the one or more optical gratings. The system further includes a controller operatively coupled to the detector, wherein the controller is configured to determine a geometric configuration of at least a portion of the shapeable instrument based on a spectral analysis of the detected reflected portions of the light signals. Variations of the devices, systems and methods described herein can employ Bragg Fiber gratings as mentioned above. However, additional variations of the devices, systems and method contained in this disclosure can employ any number of optical gratings.

In various embodiments, the optical fiber may be substantially encapsulated in a wall of the elongate instrument body. Alternatively, the elongate instrument body may define an interior lumen, wherein the optical fiber is disposed in the lumen. Further alternatively, the optical fiber may be disposed in an embedded lumen in a wall of the elongate instrument body.

In various embodiments, the elongate instrument body has a neutral axis of bending, and the optical fiber is coupled to the elongate instrument body so as to be substantially aligned with the neutral axis of bending when the elongate instrument body is in a substantially unbent configuration, and to move relative to the neutral axis of bending as the elongate instrument body undergoes bending. In other embodiments, the optical fiber is coupled to the elongate instrument body so as to be substantially aligned with the neutral axis of bending regardless of bending of the elongate instrument body. In still further embodiments, the optical fiber is coupled to the elongate instrument body so as to remain substantially parallel to, but not aligned with, the neutral axis of bending regardless of bending of the elongate instrument body.

One variation of a system may include three or more optical fibers. The fibers may have a bonded region to support strain transfer between the optical fibers and each of the optical fibers may have a fiber grating on each of the optical fibers along the bonded region.

In certain variations, the bonded region of the fibers may be tapered and/or fusion bonded and/or configured such that a bend of an optical fiber may be determined by measuring a spectral profile of a reflection from the fiber grating bonded region. The fibers may be drawn and heated to establish a tapered bonded region wherein the surfaces of the fibers are bonded for strain transfer between the fibers. Each of the optical fibers may have a fiber grating written into the same position on each of the optical fibers along the bonded region. Various features and properties of the fibers may include the following. A plurality of fiber gratings of different wavelengths may be written into the bonded region. A chirped fiber grating may be written into the bonded fiber region. Low reflectivity fiber gratings of substantially the same wavelength may be written into the bonded region. The bonded region may have a cleaved end and the cleaved end may include an antireflection coating. The cleaved end may be melted to form a nonreflecting end. The cleaved end may be angled.

A fiber grating may be angled or tilted to support, measure or allow for twist measurements. The fiber grating may be a birefringent fiber grating to support measure or allow for twist measurements. The optical fibers may be polarization preserving optical fibers. The polarization preserving optical fibers may be elliptical core optical fibers. The polarization preserving optical fibers may have at least one flattened side. The system may include an end region where the optical fibers are mechanically independent such that the fibers can be interfaced to connectors or spliced. The bonded region may be configured such that when light is coupled into any one of the optical fibers there is minimal or no cross coupling in the bonded region between any of the optical fibers. The optical fibers may extend along an axis of an elongate member or instrument of a surgical system for sensing the bend and/or twist of the elongate member and the elongate member may be manually or robotically controlled.

Another variation of a system may include a large core optical fiber. A fiber grating may be written onto said optical fiber. A light source may be provided for illuminating the fiber grating and a spectral read out system may measure a property of a reflection of light from the fiber grating The large core optical fiber may have a diameter of greater than 20 microns. The shape measuring system may also include a light source for illuminating the fiber grating. A bend of the optical fiber may be determined by measuring a spectral profile of the reflection from the fiber grating. The fiber grating may be an angled or tilted fiber grating to support twist measurements. An effective period or spacing of the fiber grating may vary across the core of the optical fiber. The optical fiber may have an index of refraction gradient across its core, which may be linear. The optical fiber may have a birefringent axes. The optical fiber may have index of refraction gradients along each birefringent axis. The optical fiber may have one or more tilted fiber gratings. The tilted fiber grating may be written along an axis that is not on one of the birefringent axes. The fiber grating may be a birefringent fiber grating that can support twist measurements. The optical fiber may extend along an axis of an elongate member instrument of a surgical system for sensing the bend and/or twist of the elongate member, which may be manually or robotically controlled.

A variation of a system for measuring twist may include a light beam director, and an optical fiber having a first reference tilted fiber grating, a second tilted fiber grating and an end reflector. The system may include a polarizer and a spectrometer or spectral read out system. The light beam director may be configured to receive a light beam such that at least a portion of the light beam is directed from the light beam director into the optical fiber. The end reflector may be configured to reflect the light beam back through a tilted fiber grating to the light beam director, through a polarizer and onto a spectrometer or other spectral read out system to measure twist along the optical fiber at points associated with a tilted fiber grating.

A polarization state of a wavelength associated with a fiber grating may be detected such that twist along a region of the fiber associated with the fiber grating can be measured. The light beam director may be a directional coupler having a first port, second port and an output port, and the system may also include a light source adapted to couple the light beam into the first port of the directional coupler. The portion of the light beam may be directed by the second port of the directional coupler into the optical fiber. The end reflector may reflect the light beam back through the tilted fiber gratings to the directional coupler where the light beam is directed by the output port of the directional coupler through a polarizer and onto a spectrometer or spectral read out system.

The beam director may be a directional coupler. The optical fiber may have an array of second tilted fiber gratings. The end reflector may be a metallic coating. Optionally, the end reflector may be a dielectric coating of one or more layers. The end reflector may be a directional coupler with a fiber loop connecting two coupler ports of the end reflector directional coupler. An output port of the light beam director may be configured to direct the light beam to a polarizing beamsplitter. The polarizing beamsplitter may have two outputs which are directed to a 2×1 switch, the 2×1 switch having an output directed to an output spectrometer. An output port of the light beam director may be configured to direct the light beam to a polarizing beamsplitter. The polarizing beamsplitter may have two outputs which are directed to a first output spectrometer and a second output spectrometer. The optical fiber may extend along an axis of an elongate member or instrument of a surgical system for sensing the twist of the elongate member. The elongate member may be manually or robotically controlled.

A method for measuring twist along a fiber may include the following steps: coupling a light beam into a light beam director; directing at least a portion of the light beam from the light beam director into an optical fiber, the optical fiber having a first reference tilted fiber grating, a second tilted fiber grating and an end reflector; reflecting the light beam back through the tilted fiber gratings to the light beam director, through a polarizer and onto a spectrometer; and detecting a polarization state of a wavelength associated with a fiber grating to measure twist along a region of the fiber associated with the fiber grating.

Another variation of a system may include a light beam director, an optical fiber having a birefringent fiber grating, a polarizer, and a spectrometer or spectral read out system. The light beam director may be configured to receive a light beam such that at least a portion of the light beam is directed from the light beam director to the birefringent fiber grating of the optical fiber. The birefringent fiber grating can at least partially reflect the light beam back to the light beam director, through a polarizer and onto a spectrometer to measure twist along the optical fiber.

The birefringent fiber grating may be polarization dependent and the polarization state of the reflected light beam may be detected to measure twist. A reflection spectra of the fiber grating may be split into two distinct spectral peaks that are polarization dependent where the relative amplitudes of the spectral peaks and/or change in their ratio can be used to measure twist. The light beam director may be a circulator. The circulator may have a first port, second port and an output port. The system may also include a light source adapted to couple the light beam into the first port of the circulator. A least a portion of the light beam may then be directed by the second port of the circulator into the birefringent fiber grating of the optical fiber. The birefringent fiber grating may at least partially reflect the light beam back to the circulator where the light beam is directed by the output port of the circulator through a polarizer and onto a spectrometer or spectral read out system.

The light beam director may be a fused biconical taper. The optical fiber may be a low birefringence optical fiber and the birefringent grating may be written onto the optical fiber. The optical fiber may along an axis of an elongate member or instrument of a surgical system for sensing the twist of the elongate member. The elongate member may be manually or robotically controlled.

A method for measuring twist along a fiber may include the following steps: coupling a light beam into a light beam director; directing at least a portion of the light beam from the light beam director into an optical fiber, the optical fiber having a birefringent fiber grating; reflecting at least a portion of the light beam off of the birefringent fiber grating toward the light beam director, through a polarizer and onto a spectrometer; splitting a reflection spectra of the fiber grating into two distinct spectral peaks that are polarization dependent; and detecting the relative amplitudes of the spectral peaks and change in their ratio to measure twist along the fiber.

Another variation of a system may include an optical fiber having a birefringent axes. A first fiber grating may be written on the optical fiber such that two effective fiber gratings are established one on each of the birefringent axes which allow for the measurement of bend.

The optical fiber may have an index of refraction gradient across each of the birefringent axes. The index of refraction gradient may be induced by exposure to light. A second fiber grating may be a tilted or angled fiber grating written on the optical fiber which allows for the measurement of twist. The titled fiber grating may be written on an axis other than the birefringent axes, e.g., between the birefringent axes. The titled fiber grating may be written on the optical fiber at a wavelength that differs from the wavelength of the first fiber grating. In certain variations, the first fiber grating may be an angled or tilted fiber grating that supports or allows for twist measurements. The optical fiber may extend along an axis of an elongate member or instrument of a surgical system for sensing the bend and/or twist of the elongate member, which may be manually or robotically controlled. In certain variations, the fiber systems described herein may be utilized or incorporated along an axis of a manual or robotically controlled elongate member or instrument of a surgical system or other medical device or instrument for sensing or measuring the shape, position, twist, roll, deflection, displacement or bend of the elongate member in a patient's body.

A method of sensing a shape of an elongate member to facilitate navigation of the elongate body in a subject's body may include: positioning an optical fiber along an axis of the elongate member or instrument, wherein the fiber has a fiber grating written thereon; and detecting bend or twist of the elongate member by measuring a spectral profile or polarization state of a reflection from the fiber grating. The method may allow for the detection of twist of the elongate member by measuring a change in a polarization state of light reflected from a fiber grating written on an optical fiber. Optionally, three optical fibers may be positioned along an axis of the elongate member, wherein the fibers have a bonded region and each of the optical fibers has a fiber grating located on each of the optical fibers along the bonded region to allow for the measurement of bend or twist.

In addition to the various medical devices, instruments and catheter applications described above, the variations of shape sensing or measuring systems including fibers, e.g., optical fibers, fiber optics, fiber optic waveguides, configured to enable measurement or sensing of position or orientation along a fixed length, described herein, may be used in a variety of other applications and in a variety of other industries. Such uses may include but are not limited to, positioning of robotic probes; determining the position of aerospace structures such as wings during testing and in flight; and determining the position of towed arrays for seismic exploration and orientation of a drill bit relative to a known position on a drill string. Other applications include to measure strain in or position of structures such as highway bridges and aircraft wings, and temperatures in structures such as supply cabinets.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

I claim:

1. A shape measuring system comprising:
   a large core optical fiber wherein a fiber grating is written onto said optical fiber; and
   a spectral read out system configured to measure a property of a reflection of light from the fiber grating,
   wherein the optical fiber includes a fiber core and a fiber cladding, and wherein a separation between outer opposite edges of the diameter of the fiber core is configured such that when the optical fiber is bent, a strain difference exists between the outer opposite edges across the fiber core, and wherein the strain difference in the optical fiber is used to determine bend and/or twisting measurements of the optical fiber.

2. A shape measuring system according to claim 1, wherein the large core optical fiber has a diameter of greater than 20 microns.

3. A shape measuring system according to claim 1, further comprising a light source for illuminating the fiber grating.

4. A shape measuring system according to claim 1, wherein a bend of the optical fiber may be determined by measuring a spectral profile of the reflection.

5. A shape measuring system according to claim 1, wherein the fiber grating is an angled or a tilted fiber grating to support twist measurements.

6. A shape measuring system according to claim 1, wherein an effective period or spacing of the fiber grating varies across the core of the optical fiber.

7. A shape measuring system according to claim 1, wherein the optical fiber has an index of refraction gradient across its core.

8. A shape measuring system according to claim 7, wherein the index of refraction gradient is linear.

9. A shape measuring system according to claim 8, wherein the optical fiber has birefringent axes.

10. A shape measuring system according to claim 9, wherein the optical fiber has index of refraction gradients along each birefringent axis.

11. A shape measuring system according to claim 10, wherein the optical fiber has at least one tilted fiber grating.

12. A shape measuring system according to claim 11, wherein the tilted fiber grating is written along an axis that is not on one of the birefringent axes.

13. A shape measuring system according to claim 1, wherein the fiber grating is a birefringent fiber grating to support twist measurements.

14. A shape measuring system according to claim 1, wherein the optical fiber extends along an axis of an elongate member of a surgical system for sensing the bend and/or twist of the elongate member.

15. A shape measuring system according to claim 14, wherein the elongate member is manually or robotically controlled.

16. A system for measuring twist comprising:
   a light beam director;
   an optical fiber having a first reference tilted fiber grating, a second tilted fiber grating and an end reflector, wherein the optical fiber has birefringent axes and wherein the first reference tilted fiber grating is positioned at a location where twist of the optical fiber is known, and wherein the second tilted fiber grating is disposed along an axis that is between the birefringent axes;
   a polarizer; and
   at least one output spectrometer,
   wherein the light beam director is configured to receive a light beam such that at least a portion of the light beam is directed from the light beam director into the optical fiber, the end reflector being configured to reflect the at least a portion of the light beam back through the tilted fiber gratings to the light beam director, through the polarizer and onto the at least one output spectrometer to detect a polarization state of a wavelength associated with the second tilted fiber grating to measure twist along the optical fiber at points associated with the second tilted fiber grating.

17. The system of claim 16, wherein the light beam director is a directional coupler having a first port, second port and an output port, and the system further comprises a light source adapted to couple the light beam into the first port of the directional coupler, wherein at least a portion of the light beam is directed by the second port of the directional coupler into the optical fiber, the end reflector being configured to reflect the light beam back through the tilted fiber gratings to the directional coupler where the light beam is directed by the output port of the directional coupler through the polarizer and onto the at least one spectrometer.

18. The system of claim 16, wherein the light beam director is a directional coupler.

19. The system of claim 16, wherein the optical fiber has an array of second tilted fiber gratings.

20. The system of claim 1, wherein the end reflector is a metallic coating.

21. The system of claim 16, wherein the end reflector is a dielectric coating of one or more layers.

22. The system of claim 16, wherein the end reflector is a directional coupler with a fiber loop connecting two coupler ports of the end reflector directional coupler.

23. The system of claim 16, wherein an output port of the light beam director is configured to direct the light beam the polarizer, the polarizer having two outputs which are directed to a 2×1 switch, the 2×1 switch having an output directed to the at least one output spectrometer.

24. The system of claim 16, wherein an output port of the light beam director is configured to direct the light beam to the polarizer, the polarizer having two outputs which are directed to a first output spectrometer and a second output spectrometer.

25. The system of claim 16, wherein the optical fiber extends along an axis of an elongate member of a surgical system for sensing the twist of the elongate member.

26. The system of claim 25, wherein the elongate member is manually or robotically controlled.

27. A method for measuring twist along a fiber comprising:
coupling a light beam into a light beam director;
directing at least a portion of the light beam from the light beam director into an optical fiber, the optical fiber having a first reference tilted fiber grating, a second tilted fiber grating and an end reflector, wherein the optical fiber has birefringent axes and wherein the first reference tilted fiber grating is positioned at a location where twist of the optical fiber is known, and wherein the second tilted fiber grating is disposed along an axis that is between the birefringent axes;
reflecting the light beam back through the tilted fiber gratings to the light beam director, through a polarizer and onto at least one spectrometer; and
detecting a polarization state of a wavelength associated with the second tilted fiber grating to measure twist along a region of the fiber associated with the second tilted fiber grating.

28. The method of claim 27, wherein the light beam director is a directional coupler having a first port, second port and an output port, and the system further comprises a light source adapted to couple the light beam into the first port of the directional coupler, wherein at least a portion of the light beam is directed by the second port of the directional coupler into the optical fiber, the end reflector being configured to reflect the light beam back through the tilted fiber gratings to the directional coupler where the light beam is directed by the output port of the directional coupler through the polarizer and onto the at least one spectrometer.

29. The method of claim 27, wherein the light beam director is a directional coupler.

30. The method of claim 27, wherein the optical fiber has an array of second tilted fiber gratings.

31. The method of claim 27, wherein the end reflector is a metallic coating.

32. The method of claim 27, wherein the end reflector is a dielectric coating of one or more layers.

33. The method of claim 27, wherein the end reflector is a directional coupler with a fiber loop connecting two coupler ports of the end reflector directional coupler.

34. The method of claim 27, wherein an output port of the light beam director directs the light beam to the polarizer, the polarizer having two outputs which are directed to a 2×1 switch, the 2×1 switch having an output directed to the at least one output spectrometer.

35. The method of claim 27, wherein an output port of the light beam director directs the light beam to the polarizer, the polarizer having two outputs which are directed to a first output spectrometer and a second output spectrometer.

36. The method of claim 27, further comprising sensing twist of an elongate member of a surgical system wherein the optical fiber extends along an axis of the elongate member.

37. The system of claim 36, wherein the elongate member is manually or robotically controlled.

38. A system for measuring twist comprising:
a light beam director;
an optical fiber having a birefringent fiber grating;
a polarizer; and
a spectrometer,
wherein the light beam director is configured to receive a light beam such that at least a portion of the light beam is directed from the light beam director to the birefringent fiber grating of the optical fiber, the birefringent fiber grating being configured to at least partially reflect the light beam back to the light beam director, which directs the light beam through the polarizer and onto the spectrometer,
wherein reflection spectra of the birefringent fiber grating is split into two distinct spectral peaks that are polarization dependent;
wherein relative amplitudes of the spectral peaks are detected to measure twist along the optical fiber; and
wherein a change in the ratio of the relative amplitudes of the spectral peaks are detected to measure twist along the optical fiber.

39. The system of claim 38, wherein the birefringent fiber grating is polarization dependent and a polarization state of the reflected light beam is detected to measure twist.

40. The system of claim 38, wherein the light beam director is a circulator.

41. The system of claim 38, wherein the light beam director is a circulator having a first port, second port and an output port, and the system further comprises a light source adapted to couple the light beam into the first port of the circulator, wherein at least a portion of the light beam is directed by the second port of the circulator into the birefringent fiber grating of the optical fiber, the birefringent fiber grating at least partially reflects the light beam back to the circulator where the light beam is directed by the output port of the circulator through the polarizer and onto the spectrometer.

42. The system of claim 38, wherein the light beam director is a fused biconical taper.

43. The system of claim 38, wherein the optical fiber is low birefringence optical fiber and the birefringent grating is written onto the optical fiber.

44. The system of claim 38, wherein the optical fiber extends along an axis of an elongate member of a surgical system for sensing the twist of the elongate member.

45. The system of claim 44, wherein the elongate member is manually or robotically controlled.

46. A method for measuring twist along a fiber comprising:
coupling a light beam into a light beam director;
directing at least a portion of the light beam from the light beam director into an optical fiber, the optical fiber having a birefringent fiber grating;
reflecting at least a portion of the light beam off of the birefringent fiber grating toward the light beam director, through a polarizer and onto a spectrometer;
splitting a reflection spectra of the fiber grating into two distinct spectral peaks that are polarization dependent; and
detecting the relative amplitudes and change in their ratio to measure twist along the fiber.

47. The method of claim 46, wherein the birefringent fiber grating is polarization dependent and a polarization state of the reflected light beam is detected to measure twist.

48. The method of claim 46, wherein the light beam director is a circulator.

49. The method of claim 46, wherein the light beam director is a circulator having a first port, second port and an output port, and the system further comprises a light source adapted to couple the light beam into the first port of the circulator, wherein at least a portion of the light beam is directed by the second port of the circulator into the birefringent fiber grating of the optical fiber, the birefringent fiber grating at least partially reflects the light beam back to the circulator where the light beam is directed by the output port of the circulator through the polarizer and onto the spectrometer.

50. The method of claim 46, wherein light beam director is a fused biconical taper.

51. The method of claim 46, wherein the optical fiber is low birefringence optical fiber and the birefringent grating is written onto the optical fiber.

52. The method of claim 46, further comprising sensing twist of an elongate member of a surgical system wherein the optical fiber extends along an axis of the elongate member.

53. The method of claim 52, wherein the elongate member is manually or robotically controlled.

54. A method of sensing a shape of an optical fiber comprising:
directing at least a portion of a light beam into an optical fiber, the optical fiber having a first reference tilted fiber grating and a second tilted fiber grating, wherein the optical fiber has birefringent axes and wherein the first reference tilted fiber grating is positioned at a location where twist of the optical fiber is known, and wherein the second tilted fiber grating is disposed along an axis that is between the birefringent axes;
reflecting the light beam back through the tilted fiber gratings, through a polarizing beam splitter and onto a detector; and
detecting a degree of polarization for each wavelength associated with the second tilted fiber grating to measure twist along a region of the optical fiber associated with the second tilted fiber grating.

55. The method of claim 54, wherein a bend of the optical fiber is determined by measuring a spectral profile of the reflection from the second tilted fiber grating.

56. The method of claim 54, wherein the twist is detected by measuring a polarization state of light reflected from the second tilted fiber grating written on the optical fiber.

57. The method of claim 54, further comprising drawing down and heating three or more optical fibers to establish a bonded region wherein surfaces of the optical fibers are bonded for strain transfer between the optical fibers and writing the second tilted fiber grating on each of the optical fibers along the bonded region.

58. The method of claim 57, wherein a plurality of fiber gratings of different wavelengths are written into the bonded region.

59. The method of claim 57, wherein the bonded region has a cleaved end.

60. The method of claim 54, wherein the second tilted fiber grating is a birefringent fiber grating that supports twist measurements.

61. The method of claim 54, wherein the second tilted fiber grating is an angled or tilted fiber grating to support twist measurements.

62. The method of claim 54, wherein the optical fiber is a polarization preserving optical fiber.

63. The method of claim 54, wherein the optical fiber is a large core optical fiber having a fiber grating written onto a core of the optical fiber.

64. The method of claim 63, wherein an effective period or spacing of the second tilted fiber grating varies across the core of the optical fiber.

65. The method of claim 63, wherein the optical fiber has an index of refraction gradient across its core.

66. The method of claim 54, further comprising:
sensing a shape of an elongate member of a surgical system to facilitate navigation of the elongate member in a subject's body comprising:
positioning the optical fiber along an axis of the elongate member; and
detecting bend or twist of the elongate member by measuring a property of a reflection of light from the second tilted fiber grating.

67. The method of claim 66, wherein three optical fibers are positioned along an axis of the elongate member, wherein the fibers have a bonded region and each of the optical fibers has a fiber grating located on each of the optical fibers along the bonded region.

68. The method of claim 66, wherein the optical fiber has a cleaved end positioned at the distal end of the elongate member.

* * * * *